United States Patent
Ley et al.

(10) Patent No.: US 9,144,248 B2
(45) Date of Patent: Sep. 29, 2015

(54) CINNAMAMIDES AS SAVORY FLAVORINGS

(75) Inventors: Jakob Peter Ley, Holzminden (DE); Katharina Reichelt, Holzminden (DE); Susanne Paetz, Höxter (DE); Michael Backes, Holzminden (DE); Katja Obst, Holzminden (DE)

(73) Assignee: SYMRISE AG, Holzminden (DE)

( * ) Notice: Subject to any disclaimer, the term of this patent is extended or adjusted under 35 U.S.C. 154(b) by 482 days.

(21) Appl. No.: 13/480,731

(22) Filed: May 25, 2012

(65) Prior Publication Data

US 2012/0308703 A1    Dec. 6, 2012

Related U.S. Application Data

(60) Provisional application No. 61/491,548, filed on May 31, 2011.

(30) Foreign Application Priority Data

May 31, 2011    (EP) .................................... 11168310

(51) Int. Cl.
| | |
|---|---|
| A23L 1/22 | (2006.01) |
| A23L 1/226 | (2006.01) |
| C11B 9/00 | (2006.01) |
| A23L 2/56 | (2006.01) |
| A61K 8/42 | (2006.01) |
| C07C 233/00 | (2006.01) |
| A23L 1/228 | (2006.01) |
| A23L 1/227 | (2006.01) |

(52) U.S. Cl.
CPC .............. *A23L 1/22091* (2013.01); *A23L 1/22* (2013.01); *A23L 1/226* (2013.01); *A23L 1/227* (2013.01); *A23L 1/228* (2013.01); *A23L 1/22671* (2013.01); *A23L 2/56* (2013.01); *A61K 8/42* (2013.01); *C07C 233/00* (2013.01); *C11B 9/0069* (2013.01); *A23V 2200/15* (2013.01); *A23V 2200/16* (2013.01)

(58) Field of Classification Search
CPC ....... A23L 1/22; A23L 1/226; A23L 1/22671; A23L 1/227; A23L 1/228; A23L 1/22091; A23L 2/56; A61K 8/42; A23V 2200/15; A23V 2200/16; C07C 233/00; C11B 9/0069
USPC .................. 426/534, 536, 538, 650
See application file for complete search history.

(56) References Cited

U.S. PATENT DOCUMENTS

| | | | |
|---|---|---|---|
| 7,476,399 B2 * | 1/2009 | Tachdjian et al. | 424/439 |
| 2003/0152682 A1 | 8/2003 | Ley et al. | |
| 2004/0202619 A1 | 10/2004 | Dewis et al. | |

FOREIGN PATENT DOCUMENTS

| | | |
|---|---|---|
| CN | 101203142 A | 6/2008 |
| CN | 101400336 A | 4/2009 |
| CN | 101422229 A | 5/2009 |
| CN | 101426381 A | 5/2009 |
| CN | 100577037 C | 1/2010 |
| EP | 1323356 * | 7/2003 |
| EP | 2064959 A1 | 6/2009 |

OTHER PUBLICATIONS

Bassard, J E et al., "Phenolamdies: Bridging polyamines to the phenolic metabolism," Phytochemistry, vol. 71, No. 16, pp. 1808-1824, 2010.
Adesina, S K et al., "Amides From Zanthoxylum Rubescens," Phytochemistry, vol. 28, No. 3, pp. 839-842, 1989.
Extended European Search Report, EP Application No. 11 168 310.8, dated Nov. 16, 2011.
Examination Report, Chinese Application No. 201210177529.1, issued on Dec. 24, 2014.
Search Report, Chinese Application No. 201210177529.1, issued on Dec. 16, 2014.

* cited by examiner

*Primary Examiner* — Leslie Wong
(74) *Attorney, Agent, or Firm* — Novak Druce Connolly Bove + Quigg

(57) ABSTRACT

The use is described of a compound of Formula (I)

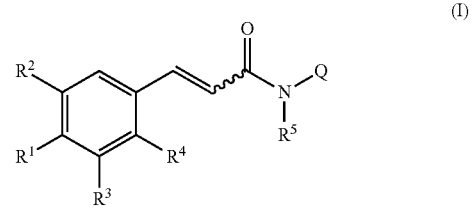

As a flavoring or flavoring mixture for imparting, modifying and/or enhancing one, two or all the taste impressions umami, kokumi and salty. Flavoring mixtures, vegetable extracts and preparations according to the invention and associated uses and methods are also described.

16 Claims, 3 Drawing Sheets

CINNAMAMIDES AS SAVORY FLAVORINGS

CROSS-REFERENCE TO RELATED APPLICATIONS

This application claims priority under 35 U.S.C. §119(e) to U.S. provisional application No. 61/491,548, filed May 31, 2011 and European Application No. 11168310.8, filed on May 31, 2011, the entire contents of which is hereby incorporated by reference.

The present invention relates to the use of compounds of Formula (I) shown below or mixtures comprising or consisting of two or a plurality of compounds of Formula (I) as a flavoring or flavoring mixture for imparting, modifying and/or enhancing one, two or all the taste impressions umami, kokumi and salty,

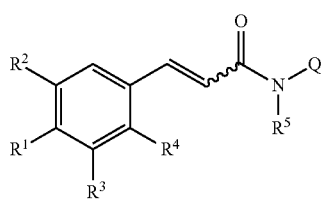

(I)

wherein for the or each compound of Formula (I) regarding the significance of the radicals or groups $R^1$ through $R^5$ and Q that stated in the following description and in the claims applies.

The present invention also relates to flavoring mixtures comprising or consisting of one or a plurality of compound(s) to be used according to the invention of Formula (I) and one, two, three or a plurality of further flavorings for imparting, modifying and/or enhancing one, two or all the taste impressions umami, kokumi and salty, wherein the further flavoring substance(s) is/are not a compound/compounds of Formula (I).

The present invention also relates to a vegetable extract comprising or consisting of one or a plurality of compound(s) to be used according to the invention of Formula (I) and one or a plurality of further components, wherein the total quantity of compounds of Formula (I) in relation to the total weight of the vegetable extract is in the range 1 000 through 500 000 ppm, preferably in the range 10 000 through 100 000 ppm. The present invention also relates to the use of such an extract for imparting, modifying and/or enhancing one, two or all the taste impressions umami, kokumi and salty.

Furthermore, the present invention relates to (ready-to-use or ready-to-serve) preparations for nutrition or pleasure, comprising or consisting of one or a plurality of components suitable for consumption, which are not compounds of Formula (I), and one or a plurality of compound(s) of Formula (I) or a flavoring mixture according to the invention or a vegetable extract according to the invention.

Furthermore, the present invention also relates to semi-finished goods for preparing a preparation for nutrition or pleasure, preferably a preparation according to the invention.

Further aspects of the present invention can be inferred from the following description, the examples, the figures and the attached claims.

There is a constant need to discover new flavorings, i.e. taste-giving compounds or compounds that are able to impart, modify and/or enhance a taste impression. There is in particular a need for compounds which are able to impart (generate), modify and/or enhance the umami and/or kokumi taste impression. Consistent with the increasing health awareness of consumers, compounds are also sought which are able to impart, modify and/or enhance a salty taste. So, all in all, there is a particular need for savory flavorings, which are able to impart, modify and/or enhance all the tastes umami, kokumi and salty. Particular preference is in general for flavorings that can be found in, and in the ideal cases isolated from, natural, fresh or dried sources, or optionally sources that can be processed using the normal methods of food preparation (e.g. evaporation or pervaporation, extraction, steaming, heating, roasting, cooking, baking, cooling, grinding, enzymatic treatment, fermentation, etc.) of animal, vegetable, fungal or microbial origin (naturally occurring substances).

A savory taste is understood in particular to be the taste known as umami of amino acids, glutamic acid and aspartic acid and the nucleotides adenosine-5'-monophosphate, cytidine-5'-monophosphate, inosine-5'-monophosphat, guanosine-5'-monophosphate, in particular in the form of their monosodium salts, in particular also in mixtures of the abovementioned substances, wherein the umami taste impression can also be brought about by other compounds that are not listed here. The umami taste impression is often described with terms such as "broth-like", "meaty", "mouth-filling" and "savory" and is often seen in combination with the kokumi taste impression. In addition the umami taste impression frequently adds to the overall saltiness of a taste, although saltiness is in particular caused by sodium ions, above all in the form of sodium chloride. The amino acids and nucleotides or salts mentioned above have the disadvantage that a relatively high concentration of these substances has to be used, in order to impart a satisfactory umami or kokumi taste impression. Thus for example monosodium glutamate regularly has to be present in a concentration of 0.02 through 0.5 wt. %, in relation to the total weight of the foodstuff, in order to generate the desired taste. The abovementioned nucleotides are also very weak in their effectiveness on their own and therefore frequently only in conjunction with monosodium glutamate can they impart a satisfactory umami taste impression.

Only in recent years have a number of (non-naturally occurring) compounds with a significantly more powerful umami-like effect been described, e.g. in the publications EP 1,989,944, WO 2008/046,895, EP 2,168,442, US2004/202, 760, US 2006/057,268 and US 2007/134,389. These compounds are said to frequently have a flavoring effect that is between 10 and 10 000 times stronger than that of monosodium glutamate.

Through molecular biological methods it has also been possible to identify the main receptor in humans that is responsible for the glutamate and umami taste. On the basis of this knowledge in WO 2003/004,992 and WO 2003/001,876 measurement methods were proposed, in order to identify possibly new sensorially effective umami flavorings. Thus in publication US 2005/084506 a number of potential activators of the umami receptor in the form of non-naturally occurring amides are described. In examples D16 (page 120 of US 2005/084506) and 81 (page 67 of US 2005/084506) non-naturally occurring cinnamamides of aromatic amines are described which allegedly are able to activate the externally expressed human, potential umami receptor.

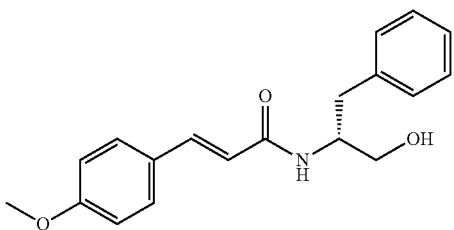

Example 81 from US 2005/084506

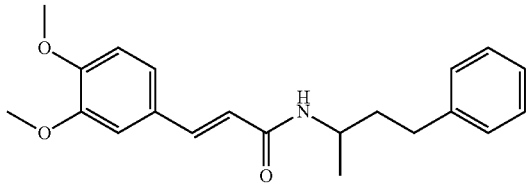

Example D16 from US 2005/084506

The abovementioned compounds are non-naturally occurring compounds. Generally—as also in connection with the present invention—however, naturally occurring compounds are preferred to synthetic or non-naturally occurring compounds. Naturally occurring amides of the abovementioned structure types imparting or enhancing a potent umami taste have not thus far been described in the prior art, however.

Although publication EP 1323356 describes the use of certain naturally-occurring cinnamamides of aromatic amines as flavorings, EP 1323356 merely discloses in this respect that these compounds (in the concentrations described there) are perceived as tangy or warming, meaning that they impart a certain chemaesthetic stimulation. None of the (primary) taste impressions imparted by the compounds described in EP 1323356 are described therein, however.

Consequently, the primary object of the present invention was to provide new applications of preferably naturally occurring compounds as flavorings for imparting, modifying and/or enhancing one, two or all the taste impressions umami, kokumi and salty. Particular preference was to indicate applications wherein compounds are used which have a 10-times stronger taste effect than monosodium glutamate.

A further object of the present invention was to indicate new flavoring mixtures.

In the context of the present invention it was particularly desirable, for the purposes of the present invention, to identify compounds that occur naturally and for example can be prepared in the form or as a component of a vegetable extract. Accordingly, a further object of the present invention was the preparation of such vegetable extracts.

Further, new (ready-to-use or ready-to-serve) preparations for nutrition or pleasure, and semi-finished products for the preparation thereof were to be provided. Monosodium glutamate-reduced or -free preparations are particularly preferred here.

Further problems for the invention can be inferred from the present description, the examples and in particular the attached claims.

The primary object of the present invention is achieved according to the invention by the use of a compound of Formula (I)

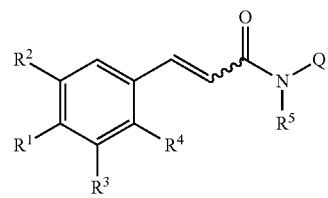

(I)

or a mixture comprising or consisting of two or a plurality of compounds of Formula (I), wherein for the or each compound of Formula (I) the following applies:
$R^1$ and $R^2$ in each case represent a methoxy group
or
$R^1$ and $R^2$ together form a —O—CH$_2$—O— group
or
$R^1$ and $R^2$ in each case represent hydrogen,
$R^3$ and $R^4$ in each case independently of one another represent hydrogen, a hydroxy group or a methoxy group,
$R^5$ represents hydrogen or a methyl group,
Q represents a group

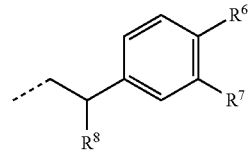

wherein
$R^6$ and $R^7$ in each case represent a methoxy group or together form a —O—CH$_2$—O— group
and $R^8$ represents hydrogen, a hydroxy group or a methoxy group,
or Q represents a group

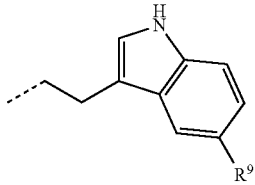

wherein
$R^9$ represents hydrogen, a hydroxy group or a methoxy group,
as a flavoring or flavoring mixture for imparting, modifying and/or enhancing one, two or all the taste impressions umami, kokumi and salty.

According to a preferred configuration of the use according to the invention all radicals $R^1$ through $R^4$ of the or one, a plurality of or all compounds of Formula (I) represent hydrogen.

Particularly preferred according to the invention is a use (as described above), wherein for the or one, a plurality of or all compounds of Formula (I) the following applies:
$R^1$ and $R^2$ in each case represent a methoxy group
or
$R^1$ and $R^2$ together form a —O—CH$_2$—O— group
or
$R^1$ and $R^2$ in each case represent hydrogen, $R^3$ and $R^4$ in each case independently of one another represent hydrogen,
$R^5$ represents hydrogen or a methyl group,
Q represents a group

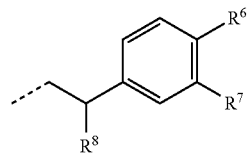

wherein
$R^6$ and $R^7$ in each case represent a methoxy group or together form a —O—CH$_2$—O— group
and $R^8$ represents hydrogen.

Preferably the or one, a plurality of or all the compounds to be used according to the invention of Formula (I) are naturally occurring compounds, in particular naturally occurring cinnamamides of aromatic amines.

The compounds of Formula (I) described in the context of this text can be present as (Z)- or (E)-isomers or as a mixture of these.

Where $R^8$ is not hydrogen, the naturally occurring cinnamamides or aromatic amines can also occur as (R)- or (S)-isomers or as a mixture of these.

Particularly preferred according to the invention is a use (as described above), wherein the compound of Formula (I) or one, a plurality of or (preferably) all the compounds of Formula (I) is or are selected from the group consisting of compound (1) of formula

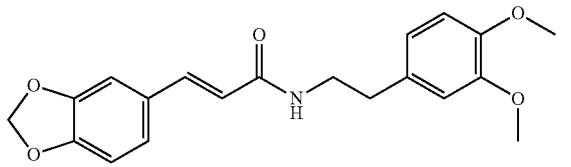 [SMILES: COc1ccc(CCNC(=O)/C=C/c2ccc3c(c2)OCO3)cc1OC]

compound (2) of formula

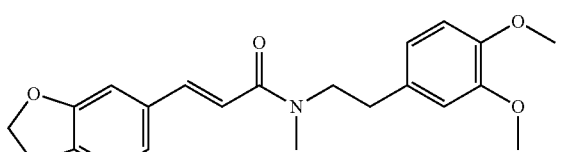

compound (3) of formula

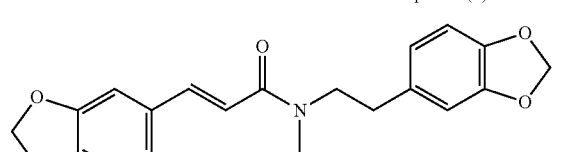

compound (4) of formula

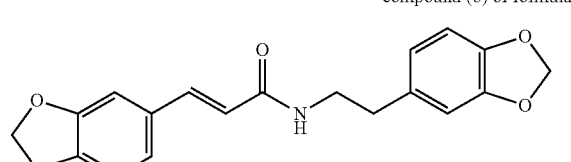

, compound (5) of formula

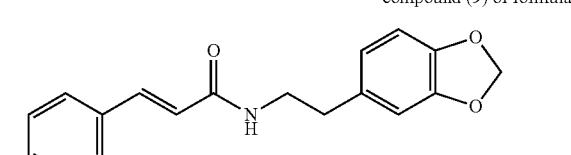

, compound (6) of formula compound (7) of formula compound (8) of formula compound (9) of formula

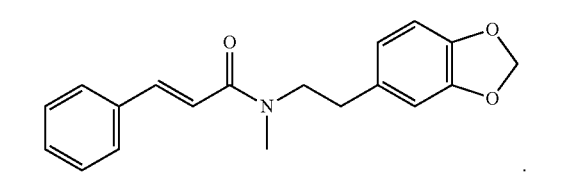

and compound (10) of formula

The abovementioned compounds (1) through (10), in particular compounds (1) and (3), are particularly suitable for the purposes of the present invention.

An overview of naturally occurring cinnamamides of aromatic amines can be found, by way of example, in Chapter 3 of the review article by Bassard, J.-E.; Ullmann, P.; Bernier, F.; Werck-Reichhart, D., *Phytochemistry* 2010, 71, (16), 1808-1824.

The (naturally occurring) compounds (1) through (10) particularly preferred for the purposes of the present invention are known from the following publications:

| Compound | Structure | Source | Publication |
|---|---|---|---|
| Compound (1) (rubemamine) | 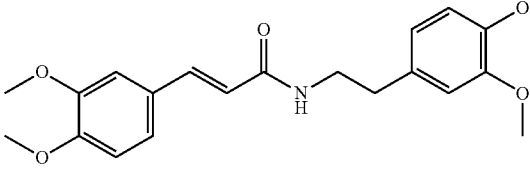 | *Zanthoxylum rubescens* (Traces) | S.K. Adesina and J. Reisch, *Phytochemistry* 1989, 28 (3), 839-842 |
| | | *Chenopodium album* (5-10 mg/kg) | Cutillo, F.; D'Abrosca. B.; DellaGreca, M.; Di Marino, C; Golino, A.; Previtera, L.; Zarrelli, A. *Phytochemistry* 2003, 64, 1381-1387 |
| Compound (2) (rubemamide) | 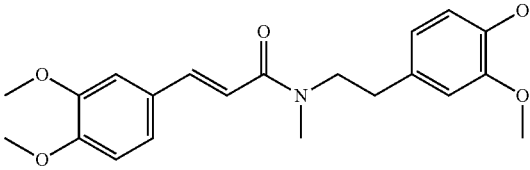 | *Zanthoxylum rubescens* | S.K. Adesina and J. Reisch, *Phytochemistry* 1989, 28 (3), 839-842 |
| Compound (3) (rubescenamine) | 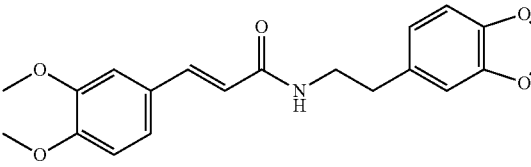 | *Zanthoxylum rubescens* | S.K. Adesina, *Planta Medica* 1989, 55 (3), 324-326 |
| Compound (4) (rubescenamide) | 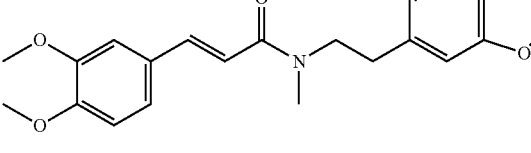 | *Zanthoxylum rubescens* | S.K. Adesina, *Planta Medica* 1989, 55 (3), 324-326 |
| Compound (5) (zanthosine) | 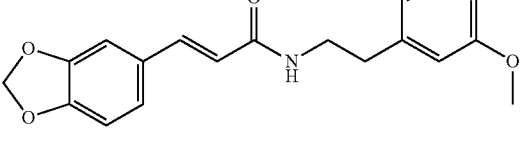 | *Zanthoxylum rubescens* | S.K. Adesina, *Planta Medica* 1989, 55 (3), 324-326 |
| Compound (6) (zanthosinamide) | 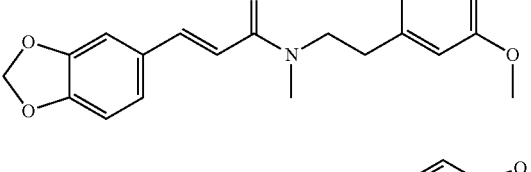 | *Zanthoxylum rubescens* | S.K. Adesina, O.A. Olatunji, D. Bergenthal and J. Reisch, *Pharmazie* 1988, 43 (7), 517-518 |
| Compound (7) (dioxamide) | 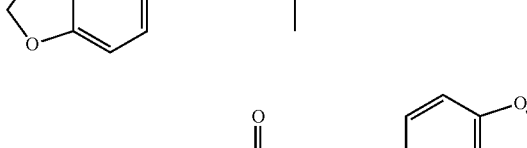 | *Zanthoxylum rubescens* | S.K. Adesina and J. Reisch, *Phytochemistry* 1989, 28 (3), 839-842 |
| Compound (8) (dioxamine) | 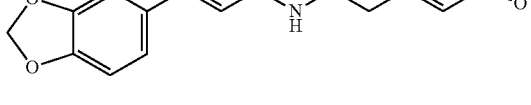 | *Zanthoxylum rubescens* | S.K. Adesina and J. Reisch, *Phytochemistry* 1989, 28 (3), 839-842 |

-continued

| Compound | Structure | Source | Publication |
|---|---|---|---|
| Compound (9) (zanthomamine) | 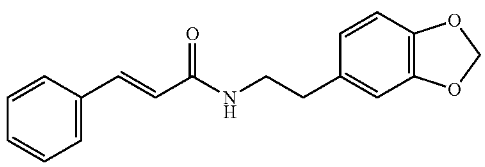 [SMILES: O=C(/C=C/c1ccccc1)NCCc1ccc2c(c1)OCO2] | *Zanthoxylum rubescens* | S.K. Adesina and J. Reisch, *Phytochemistry* 1989, 28 (3), 839-842 |
| Compound (10) (zanthomamide) | 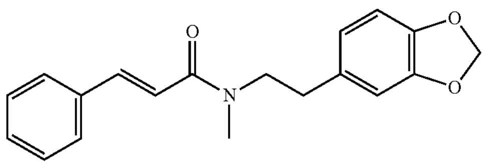 [SMILES: CN(CCc1ccc2c(c1)OCO2)C(=O)/C=C/c1ccccc1] | *Zanthoxylum rubescens* | S.K. Adesina and J. Reisch, *Phytochemistry* 1989, 28 (3), 839-842 |

In particular in consideration of publication EP 1323356 already mentioned by way of introduction, it was surprising that the compounds to be used according to the invention of Formula (I) or the mixtures to be used according to the invention (contrary to expectation according to EP 1323356) at higher concentrations still only impart or generate a sub-threshold chemaesthetic stimulation, but for this reason in highly monosodium glutamate-reduced and in monosodium glutamate-free foodstuffs and in foodstuffs with a reduced sodium chloride content (for example in savory foods such as tomato soup, chicken soup, breadsticks, frozen pizza, potato chips and popcorn) both in the initial flavor (impact) and in the longer-lasting taste perception in particular are able to impart, modify and/or enhance an umami taste. The additional advantageous feature discovered by us in the context of our own investigations, of compounds of Formula (I) to be used according to the invention, in particular compounds of Formula (I) (as described above) to be preferably used according to the invention, in addition to imparting, modifying and/or enhancing a salty taste (similar to monosodium glutamate), allows a taste experience that is perceived as particularly pleasant, which in many cases is even assessed as preferable to monosodium glutamate.

Particularly preferred according to the invention is an application as described above, wherein the compound of Formula (I) or both compounds (I) or one or two of the compounds of Formula (I) is or are selected from the group consisting of

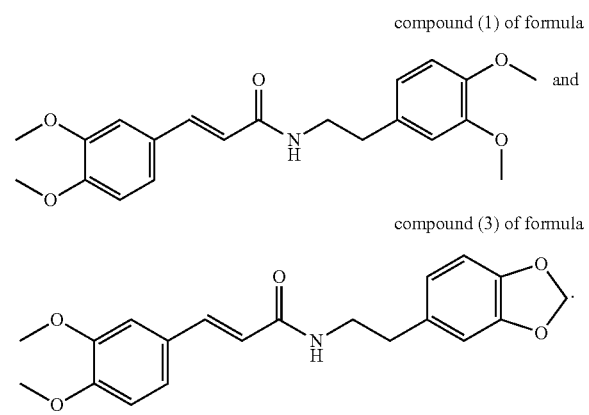

compound (1) of formula and compound (3) of formula

Particularly preferred in addition is the use of a mixture (as described above), wherein the mixture comprises or consists of both a compound (1) (as described above) and a compound (3) (as described above). A mixture provided in the context of the present invention comprising or consisting of a compound (1) and a compound (3) (as described, respectively, above) is advantageously particularly well-suited to imparting, modifying and/or enhancing one, two or all the taste impressions umami, kokumi and salty.

Compared with other compounds with an umami taste, in particular rubemamine (compound (1)) at just 10 mg/kg and rubescenamine (compound (3)) at 5 mg/kg test concentration are characterized by an umami taste that is very similar to that of monosodium glutamate (MSG), which above all enhances the mouth-fill and meaty character and the mouth-watering effect significantly, without tasting unpleasantly sweet. This is shown in the spider chart attached as FIG. 1 from Example 2, in which an American beef extract as the base was compared with (i) such a base with the addition of 10 ppm (iii) or 50 ppm rubemamine (compound (1)) (iv) and with a sample (ii) of such a base with the addition of 0.05 wt. % MSG (monosodium glutamate). In a similar experiment (shown in FIG. 2 from Example 2) compound (3), at just 5 ppm exhibits a strong effect (curve iii) and at 10 ppm (curve iv) for most descriptors is able to achieve a similarly strong assessment to sample (ii) of such a base with the addition of 0.05 wt. % MSG. The above observations will tend to apply by analogy for all compounds or mixtures to be used according to the invention.

Evidence of an enhancement of the monosodium glutamate effect is also provided by the spider chart attached as FIG. 3 from Example 3. Here (i) a beef extract as the base is compared with (ii) such a base with the addition of 0.05% monosodium glutamate, (iii) such a base with the addition of 0.0025% monosodium glutamate and (iv) such a base with the addition of 0.0025% monosodium glutamate and 20 ppm rubemamine (compound (1)). Whereas sample (iii) overall in terms of the parameters investigated was perceived only slightly less strongly than sample (i) without the addition, sample (ii) with the high glutamate content and the sample with the lower concentration of glutamate and rubemamine (iv) were hardly distinguishable from one another other than a slightly lower sweetness.

Rubescenamine (compound (3)) is advantageously also in particularly low concentration able to enhance the monosodium glutamate effect, as demonstrated by the spider chart attached as FIG. 4 from Example 3. Here again (i) a beef extract as the base is compared with (ii) such a base with the addition of 0.05% monosodium glutamate, with (iii) such a base with the addition of 0.0025% monosodium glutamate and with (iv) such a base with the addition of 0.0025% monosodium glutamate and with the addition of 5 ppm rubescenamine (compound (3)). Here also the sample with the lower concentration of glutamate and Rubescenamine (iv) in respect of virtually all parameters was assessed as stronger than sample (iii), and in particular in respect of the "salty" parameter similar to sample (ii).

In the context of the present invention a method for imparting, modifying and/or enhancing a taste selected from the group consisting of umami, kokumi and salty, is also described. Here a prepared substance or composition of a compound of Formula (I) to be used according to the invention or a mixture to be used according to the invention (as in each case described above) or a flavoring mixture according to the invention (see below) is added in an effective quantity for an umami taste. For preferred compounds of Formula (I) or mixtures to be used according to the invention and flavoring mixtures according to the invention that stated in the context of this text applied by analogy.

The present invention relates to in particular applications according to the invention (as described above) in a preparation for nutrition or pleasure. Preferred preparations are described below.

A further aspect of the present invention relates to new flavoring mixtures.

A flavoring mixture according to the invention comprises or consists of
(i) a compound of Formula (I) or a mixture comprising or consisting of two or a plurality of compounds of Formula (I), as defined in each case above, preferably those designated as preferred above,
and
(ii) one, two, three or a plurality of further flavorings for imparting, modifying and/or enhancing one, two or all the taste impressions umami, kokumi and salty, wherein the further flavoring(s) is/are not a compound or compounds of Formula (I).

In the context of the present invention it is generally the case that the compounds to be used according to the invention of Formula (I) or mixtures of these are used in applications according to the invention or as a component of flavoring mixtures, preparations or semi-finished products according to the invention preferably in combination with one, two, three or a plurality of further flavorings for imparting, modifying and/or enhancing one, two or all the taste impressions umami, kokumi and salty, wherein these further flavorings are not compounds of Formula (I).

Furthermore, the compounds to be used according to the invention of Formula (I) or mixtures of these in the context of the present invention are preferably used in combination with one or a plurality of substance(s), not corresponding to Formula (I) to mask or reduce an unpleasant taste impression (in particular a bitter, metallic, chalky, acidic and/or astringent taste impression) and/or to enhance or to impart a (further) pleasant taste impression (e.g. sweet).

Particularly preferred is or are the or two, three, a plurality of or all the further flavorings for imparting, modifying and/or enhancing the taste impressions taste impressions umami, kokumi and/or salty, which according to the invention can be combined with the compounds of Formula (I) or mixtures of these (as described above), preferably selected from the group consisting of monosodium glutamate, free glutamic acids, nucleotides or their pharmaceutically acceptable salts, strombines, theogallines, pyridin-betaine compounds, glutamic acid glycosides, malic acid glycosides, glutathione derivates, lactisoles and alkylpyridines (preferably alkylpyridines as described in WO2009 122318 and WO2009 1223319), in particular 2-hexyl-, 2-heptyl and 2-octylpyridine, (2E,6Z)-N-cyclopropylnona-2,6-dienamide, (2E,6Z)-N-ethylnona-2,6-dienamide, N-[(2E)-3,7-dimethylocta-2,6-dienyl]cyclopropane carboxamide, N'-[(2-methoxy-4-methyl-phenyl)methyl]-N-[2-(5-methyl-2-pyridyl)ethyl] oxamide, N'-[(2,4-dimethoxyphenyl)methyl]-N-[2-(2-pyridyl)ethyl]oxamide, N'-[(2-methoxy-4-methyl-phenyl) methyl]-N-[2-(2-pyridyl)ethyl]oxamide, N-(1-propylbutyl)-1,3-benzodioxole-5-carboxamide, 1-(2-hydroxy-4-isobutoxy-phenyl)-3-(2-pyridyl)propan-1-one and 1-(2-hydroxy-4-methoxy-phenyl)-3-(2-pyridyl)propan-1-one.

Generally the or two, three, a plurality of or all the further flavoring(s) for imparting, modifying and/or enhancing one, two or all the taste impressions umami, kokumi and salty is or are preferably naturally occurring compound(s), particularly preferably compounds selected from the group consisting of: monosodium glutamate, free glutamic acid, nucleotides (e.g. adenosine-5'-monophosphate, cytidin-5'-monophosphate, inosine-5'-monophosphate, guanosine-5'-monophosphate), or their pharmaceutically acceptable salts, strombines as described in WO 2010 100,589, theogallines as described in JP 2007 110,988, pyridin-betaine compounds as described in EP 1291342, glutamic acid glycosides as described in WO 2002 087361, malic acid glycosides as described in WO 2006 003107, glutathione derivates as described in EP 181421 or WO 2007 042273, lactisols, hydroxyflavanones (e.g. eriodictyol, homoeriodictyol or their sodium salts), in particular according to EP 1258200, hesperitin according to EP 1909599, phloretin according to EP 1972203 or EP 1998636, hydroxyflavanea according to US 2010 292175, 4-hydroxychalcones according to EP 1972203, extracts with a *Hydrangea dulcis* basis according to EP 2298084, or *Rubus* ssp. according to U.S. Provisional Application 61/333,435 and publications associated therewith; mixtures of milk proteins with lecithins, yeast extracts, vegetable hydrolyzates, powdered vegetables (e.g. onion powder, tomato powder), vegetable extracts (e.g. from lovage or mushrooms such as the Shiitake variety), sea algae and mineral salt mixtures, in particular mineral salt mixtures according to US 2009 214,728 and publications associated therewith.

Synthetic flavorings, preferably to be combined with compounds to be used according to the invention of Formula (I) or mixtures of these, for imparting, modifying and/or enhancing one, two or all the taste impressions umami, kokumi and salty are preferably selected from the chemical structures described in publications US 2004 0202619, US 2004 0202760, US 2006 0057268 and US 2006 0068071, in particular (2E,6Z)-N-cyclopropylnona-2,6-dienamide (FEMA 4087; Flavis 16.093), 2E,6Z)-N-ethylnona-2,6-dienamide (FEMA 4113; Flavis 16.094) and N-[(2E)-3,7-dimethylocta-2,6-dienyl]cyclopropancarboxamide (FEMA 4267; Flavis 16.095), the chemical structures as described in US2005 0084506, in particular N'-[(2-methoxy-4-methyl-phenyl)methyl]-N-[2-(5-methyl-2-pyridyl)ethyl]oxamide (FEMA 4234; Flavis 16.190), N'-[(2,4-dimethoxyphenyl)methyl]-N-[2-(2-pyridyl)ethyl]oxamide (FEMA 4233; Flavis 16.099), N'-[(2-methoxy-4-methyl-phenyl)methyl]-N-[2-(2-pyridyl) ethyl]oxamide (FEMA 4231; Flavis 16.101), N-(1-propylbutyl)-1,3-benzodioxole-5-carboxamide (FEMA 4232; Flavis 16.098), and the chemical structures as described in WO/2011/004016, in particular 1-(2-hydroxy-4-isobutoxyphenyl)-3-(2-pyridyl)propan-1-one (FEMA 4722) and 1-(2-hydroxy-4-methoxy-phenyl)-3-(2-pyridyl)propan-1-one (FEMA 4723).

In a preferred configuration of the present invention the compounds to be used according to the invention of Formula (I) or mixtures of these in the context of the application according to the invention or in flavoring mixtures according to the invention, preparations according to the invention or semi-finished products according to the invention are used in combination with one or a plurality of sweetness-enhancing substances, in particular with one or a plurality of compounds according to WO2007/014879 A1, WO 2007/107596 A1, US 2010 292,175 and EP 1955601, in particular together with hesperetine, 3,7'-dihydroxy-4'-methoxyflavane and/or phloretin. In this way advantageously an enhancement, a deepening and a rounding of the taste profile is achieved, in particular in preparations and semi finished products according to the invention with a savory and/or salty taste. The overall proportion of hesperetin, 3,7'-dihydroxy-4'-methoxyflavane and/or phloretin in such compositions or preparations is preferably (in each case) in the range 1 through 400 ppm, preferably in the range 5 through 200 ppm, in relation to the total weight of the preparation or semi-finished product.

Further flavorings to be advantageously combined with compounds to be used according to the invention of Formula (I) or mixtures and further substances are described below.

The total quantity of compounds of Formula (I) in a flavoring mixture according to the invention (as described above) is preferably in the range 0.0001 through 95 wt. %, in relation to the total weight of the flavoring mixture, particularly preferred in the range 0.001 through 95 wt. %.

Naturally occurring cinnamamides of aromatic amines of Formula (I) are often available in the natural (vegetable) sources only in extremely low quantities. Thus for example the rubemamine found in entire *Chenopodium album* (white goosefoot) plants was 5-10 mg/kg and the traces found in the bark of *Zanthoxylum rubescens* were even smaller. As a result through the use of native or dried plant parts or to some extent also the simple, not further purified extracts in ready-to-serve foodstuffs frequently a satisfactory umami effect is not achieved. One aspect of the present invention is thus also to make available naturally occurring cinnamamides of aromatic amines of Formula (I) in a sufficient concentration and purity through conventional synthesis, biomimetic/biotechnological synthesis or extraction and purification as well as optionally concentration, in order to use these in semi-finished products or ready-to-serve preparations for nutrition or pleasure in sufficient concentration (to achieve the umami taste).

A preferred aspect of the present invention relates to a vegetable extract comprising or consisting of a compound of Formula (I) or a mixture comprising or consisting of two or a plurality of compounds of Formula (I), as defined in each case above, preferably as identified above as preferred, and one or a plurality of further components, wherein the total quantity of compounds of Formula (I) in relation to the total weight of the vegetable extract is in the range 1 000 through 500 000 ppm, preferably in the range 10 000 through 100 000 ppm.

The compounds to be used according to the invention of Formula (I) are preferably naturally occurring compounds, concentrated, preferably by extraction from a plant or parts of these and optionally by conventional methods, wherein the compounds are particularly preferably those compounds of Formula (I), which are extracted from plants (or parts thereof) selected from the group consisting of *Zanthoxylum rubescens* and *Chenopodium album*.

Accordingly, a vegetable extract according to the invention (as described above) is according to a preferred aspect of the present invention an extract of *Zanthoxylum rubescens* or *Chenopodium album*.

Here such an extract preferably comprises only those further components which at a temperature of 20° C. under normal pressure are present as solid matter and more preferably are not pure amino acids, in particular not amino acids which impart an umami taste, such as for example glutamic acid and aspartic acid.

Particularly preferably the further components of an extract according to the invention are exclusively compounds, which can be extracted by means of ethanol or methanol or a methanol-ethanol-, methanol-water-, methanol-ethanol-water- or ethanol-water-mixture, supercritical carbon dioxide, ethyl acetate, tert-butyl methyl ether, dichloromethane, n-heptane, n-hexane or mixtures of these from *Zanthoxylum rubescens* or *Chenopodium album*. Here the extraction preferably takes place at temperatures in the range between −80° C. and boiling point of the extraction agent, preferably for between 5 minutes and 24 hours by simple stirring, percolation and or countercurrent extraction. The extraction in particular with aqueous mixtures can also take place in the presence of pH-regulating acids, bases or buffer mixtures.

The extracts according to the invention, in particular those from *Zanthoxylum rubescens* or *Chenopodium album*, are preferably prepared by first passing the plant parts, preferably fresh or dried above-ground parts (particularly preferably leaves, stems, flowers, barks, bast, wood and/or fruits) in dried or comminuted form through the following steps:

a) Using a suitable solvent (e.g. water, water-ethanol-mixtures, ethanol, methanol, 1-propanol, 2-propanol, glycerin, propane-1,2-diol, supercritical carbon dioxide, ethyl acetate, tert-butyl methyl ether, dichloromethane, n-heptane, n-hexane or mixtures of these) at between 0° C. and boiling point of the respective solvent, for example by stirring, the Soxhlet, countercurrent, percolation or simple screening basket method, a primary extract is extracted, wherein the solvent in each case can be used alone, in binary or ternary mixtures or also consecutively in an increasing sequence of polarity.

Preference is for a consecutive extraction method with an increasing sequence of polarity of the solvent. Here, starting with a non-polar solvent the plant parts to be extracted undergo extraction. The solvent is drawn off and the primary extract from this extraction step is obtained. Then at least in one further step the extraction from the plant parts that previously underwent extraction during the first extraction step is repeated, wherein a solvent of higher polarity is used and a corresponding primary extract is obtained from this extraction step.

The consecutive extraction here can comprise multiple extraction steps, wherein preferably the final step is performed with water, ethanol, methanol, 1-propanol, 2-propanol, glycerin, propane-1,2-diol or a mixture of one of the abovementioned anhydrous solvents with water. An extract used in preparations according to the invention (orally consumable) is preferably obtained from a primary extract from the last extraction step.

The extractions can in each case take place at temperatures of between −80° C. and the respective boiling point of the extraction agent for preferably between 5 minutes and 24 hours by simple stirring, percolation or countercurrent extraction.

b) The respective primary extract is optionally concentrated down by distillation or other evaporative or pervaporative method, optionally until only solid matter or very little volatile liquids remain.

c) Optionally the (optionally concentrated) primary extract is purified by treatment with or on adsorbents (e.g. silica gel, modified silica gel (e.g. RP phases), active charcoal, zeolites, bentonite, kieselgur, aluminum, basic or acid or neutral [macroporous] ion exchangers) in the batch or column chromatography method, optionally also with the help of further solvents, preferably water, n-hexane, dichloromethane, formic acid, methanol, ethanol, or 1,2-propylene glycol (secondary extract).

d) Optionally the secondary extract is dried by distillation or other evaporative or pervaporative method (dry extract).

e) Optionally the dried secondary extract is dissolved again in a suitable solvent or mixture (e.g. ethanol, 1,2-propylene glycol, vegetable oil triglycerides, triacetin or glycerin).

Evaporative or pervaporative methods for the purposes of the present invention are preferably distillation, sublimation, steam distillation, freeze-drying, pervaporative membrane methods and spray drying, wherein to this end prior to the respective treatment suitable excipients and carriers can be added.

The primary extract (preferably from *Zanthoxylum rubescens* or *Chenopodium album*) according to b) (see above) can also be further broken down, e.g. through enzymatic treatment (e.g. with cellulases to breakdown the cells), by treatment with acid (e.g. under pressure), by treatment with suitable basic solutions (e.g. of hydroxides, carbonates or hydrogen carbonates of sodium, potassium, calcium, magnesium and zinc), with acidic ion exchangers or with steam, preferably under pressures of 0.01 mbar through 100 bar, particularly preferably at 1 mbar through 20 bar.

The secondary extract (preferably from *Zanthoxylum rubescens* or *Chenopodium album*) according to c) can also be mixed with a proportion of 1 through 99 wt. %, in relation to the dried secondary extract, with excipients and carriers (e.g. maltodextrin, starch, natural or synthetic polysaccharides and/or vegetable gums such as modified starches or gum Arabic), in order to improve the preparation of a dry extract according to d).

In the context of the present invention preferred solvents suitable for extraction for foodstuffs and semi-luxury foods are water, ethanol, methanol, 1-propanol, 2-propanol, propane-1,2-diol, glycerin, acetone, dichloromethane, ethyl acetate, diethyl ether, hexane, heptane, triacetin, vegetable oils or fats, supercritical carbon dioxide and mixtures of these. Particularly preferred are water, ethanol, methanol, 1-propanol, 2-propanol, glycerin, propane-1,2-diol and mixtures of these, in particular mixtures of one or a plurality of the abovementioned anhydrous solvents with water, in particular for use in an extraction stage, which follows at least one extraction stage with a lower polar (preferably non-polar) solvent. For it has surprisingly transpired that with this way of consecutive extraction, in the extract of the in particular final extraction step a number or all of the distorting taste notes are no longer present.

Preferred excipients or carriers are maltodextrin, starch, natural or synthetic polysaccharides and/or vegetable gums such as modified starches or gum Arabic, solvents permitted for the aroma compositions such as for example ethanol, 1,2-propylene glycol, water, glycerin, triacetin, vegetable oil triglycerides, colorings, e.g. permitted food colorings, coloring plant extracts, stabilizers, preservatives, antioxidants and viscosity-modifying substances.

The concentrated or dried primary extract (preferably of *Zanthoxylum rubescens* or *Chenopodium album*) according to b) preferably contains 0.001 through 80 wt. % preferably 0.005 through 50 wt. %, particularly preferably 0.01 through 25 wt. %, more preferably 0.1 through 25 wt. % of compounds of Formula (I), in each case in relation to the dry weight of the concentrated primary extract.

The concentrated or dried secondary extract (preferably of *Zanthoxylum rubescens* or *Chenopodium album*) according to d) preferably contains 0.001 through 100 wt. % preferably 1 through 99 wt. %, particularly preferably 10 through 95 wt. % of the compounds of Formula (I), in each case in relation to the dry weight of the concentrated secondary extract.

The present invention also relates to the use of a vegetable extract according to the invention (as described above) for imparting, modifying and/or enhancing one, two or all the taste impressions umami, kokumi and salty.

The compounds to be used according to the invention of Formula (I) can also be obtained by (known) synthetic preparation methods (e.g. from the corresponding acids with the amines, as for example described in DE-19737327) or obtained by enzymatic (e.g. as described in WO2004 033699) or fermentative processes, which can also be carried out in plants (e.g. Negrel, J.; Javelle, F.; Paynot, M., Wound-induced tyramine hydroxycinnamoyl transferase in potato (*Solanum tuberosum*) tuber disks. *J. Plant Physiol.* 1993, 142, (5), 518-524) or Ishihara, A.; Kawata, N.; Matsukawa, Iwamura, H., Induction of N-Hydroxycinnamoyltyramine synthesis and tyramine N-Hydroxycinnamoyltransferase (THT) activity by wounding in maize leaves, Biosci. Biotechnol. Biochem. 2000, 64, (5), 1025-1031) or plant cultures.

As mentioned by way of introduction, the present invention also relates to ready-to-use or ready-to-serve preparations for nutrition or pleasure. A preparation according to the invention comprises or consists of according to a first alternative (a1) a compound of Formula (I) or a mixture comprising or consisting of two or a plurality of compounds of Formula (I), as defined above, preferably as defined above as preferred, and (b) one or a plurality of further components suitable for consumption, wherein the further component(s) is or are not a compound or compounds of Formula (I), wherein the total quantity of compounds of Formula (I) in relation to the total weight of the ready-to-use or ready-to-serve preparation is in the range 5 ppm through 500 ppm, preferably in the range 5 ppm through 200 ppm, in particular preferably in the range 5 ppm through 100 ppm.

It is particularly preferred if the total quantity of compounds of Formula (I) in relation to the total weight of the ready-to-use or ready-to-serve preparation is in the range 10 through 200 ppm, particularly preferably in the range 25 through 100 ppm.

According to a second alternative a preparation according to the invention comprises or consists of (a2) a flavoring mixture as described above or a vegetable extract as described above and (b) one or a plurality of further components suitable for consumption, wherein the further component(s) is or are not a compound or compounds of Formula (I).

For preferred compounds of Formula (I) or mixtures and for preferred configurations of the flavoring mixtures to be used or of the vegetable extract to be used in each case that stated above applies by analogy.

Preferably here the total quantity of compounds of Formula (I) in relation to the total weight of the preparation is in the range 1 ppm through 500 ppm, preferably in the range 1 ppm through 200 ppm, particularly preferably in the range 1 ppm through 100 ppm.

Preferably for a preparation according to the invention according to the second alternative described above, it is also the case that the total quantity of compounds of Formula (I) in relation to the total weight of the preparation is particularly preferably in the range 5 ppm through 500 ppm, more preferably in the range 5 ppm through 200 ppm, particularly preferably in the range 5 ppm through 100 ppm.

It is particularly preferable if the total quantity of compounds of Formula (I) in relation to the total weight of the ready-to-use or ready-to-serve preparation is in the range 10 through 200 ppm, particularly preferably in the range 25 through 100 ppm.

The ready-to-use or ready-to-serve (for nutrition or pleasure) preparations according to the invention are habitually products that are intended to be introduced into the human oral cavity, remain there for a certain time and then either be consumed (e.g. ready-to-serve foodstuffs, see also below) or removed from the oral cavity again (e.g. chewing gum). These products include all substances or products which are intended to be ingested in the processed, partially processed or unprocessed state by humans. These also include substances that are added to foodstuffs during their preparation, handling or processing and which are intended to be introduced into the human oral cavity.

In the context of the present text the term "foodstuff" means in particular substances that are intended, in the unaltered, prepared or processed state, to be swallowed and then digested by humans; in this connection foodstuffs also cover shells, coatings or other enclosures that are intended to be swallowed at the same time, or the swallowing of which can be envisaged. Certain products that are normally removed from the mouth again (e.g. chewing gum) are also understood to be foodstuffs in the context of the present text, since it cannot be excluded that these will at least in part be swallowed.

A ready-to-serve foodstuff is understood here to be a foodstuff, which in respect of the substances instrumental in the taste has already been completely put together. The term "ready-to-serve" foodstuff also covers drinks and solid or semi-solid ready-to-serve foodstuffs. By way of example deep-frozen products are mentioned, which must be thawed before consumption and heated to consumption temperature. Products such as yogurt or ice-cream, but also chewing gum or hard candies, are classified as ready-to-serve foodstuffs.

The present invention also relates to semi-finished products according to the invention for producing a preparation for nutrition or pleasure (preferably a preparation according to the invention) comprising or consisting of
(a) a compound of Formula (I) or a mixture comprising or consisting of two or a plurality of compounds of Formula (I), as defined above, preferably as defined above as preferred,
or
a flavoring mixture as described above
or
a vegetable extract as described above
and
(b) one or a plurality of further components suitable for consumption, wherein the further component(s) is or are not a compound or compounds of Formula (I),
wherein the total quantity of compounds of Formula (I) in relation to the total weight of the semi-finished product is in the range 10 ppm through 500 000 ppm, preferably in the range 25 ppm through 100 000 ppm, in particular in the range 50 ppm through 15 000 ppm.

In connection with the present text a semi-finished product means a product that because of a very high content of aroma and flavoring agents is unsuitable for use as a ready-to-serve foodstuff. Only by mixing with at least one further component (e.g. by reducing the concentration of the aroma and flavoring agents concerned) and optionally further process steps (e.g. heating, freezing) is the semi-finished product converted into a ready-to-serve foodstuff. Examples of semi-finished products here are packet soups, baking extracts and custard powder.

A number of preparations or semi-finished products according to the invention (as described above) are particularly preferred. Thus for example preparations or semi-finished products according to the invention according to a preferred embodiment are spray-dried preparations or semi-finished products, which comprise as further components suitable for consumption (inter alia) solid carriers.

Preference according to the invention is for preparations or semi-finished products according to the invention, comprising one or a plurality of carriers suitable for consumption, wherein, in relation to the dry weight of the preparation or semi-finished product, the ratio of weight of the total quantity of compounds of Formula (I) to the total quantity of solid carriers suitable for consumption is preferably in the range 1:10 through 1:100 000, preferably in the range 1:50 (preferably 1:100) through 1:20 000, particularly preferably in the range 1:100 (preferably 1:1 000) through 1:5 000.

It is more preferable here if the total quantity of compounds of Formula (I) and solid carriers suitable for consumption in relation to the total weight of the preparation or semi-finished product is in the range 70 through 100 wt. %, preferably in the range 85 through 100 wt. %.

Advantageous carriers are silicon dioxide (silicic acid, silica gel), carbohydrates and/or carbohydrate polymers (polysaccharides), cyclodextrins, starches, decomposed starches (starch hydrolyzates), chemically or physically modified starches, modified celluloses, gum Arabic, ghatti gum, tragacanth, karaya, carrageenan, guar gum, carob gum, alginates, pectin, inulin or xanthan gum. Preferred starch hydrolyzates are maltodextrins and dextrins.

Particularly preferred carriers according to the invention are silicon dioxide, gum Arabic and maltodextrins, wherein here in turn maltodextrins with DE-values in the range 5 through 20 are particularly preferred. Here it is unimportant which plants originally provided the starch for preparing the starch hydrolyzate. Particularly suitable and readily available, however, are corn-based starches and starches from tapioca, rice, wheat or potatoes. Here the carriers can act as flow agents, such as for example silicon dioxide.

The preparations or semi-finished products according to the invention, which apart from the compound(s) to be used according to the invention of Formula (I) or mixtures defined above further comprise one or a plurality of solid carriers, can for example be prepared by mechanical mixing processes, wherein at the same time comminution of the particles can take place, or by means of spray-drying. Accordingly, particular preference is for compositions or semi-finished products according to the invention, comprising solid carriers and prepared by means spray-drying; with regard to the spray-drying, reference is made to U.S. Pat. No. 3,159,585, U.S. Pat. No. 3,971,852, U.S. Pat. No. 4,532,145 or U.S. Pat. No. 5,124,162.

Preferred preparations and semi-finished products according to the invention, containing carriers, prepared by means of spray drying, have an average particle size in the range 30 through 300 μm and a residual moisture of less than or equal to 5 wt. %.

A flavoring mixture according to the invention, preparation according to the invention or semi-finished product according to the invention (as described in each case above) comprises, according to a preferred aspect of the present invention—in addition to the compounds of Formula (I)—one or a plurality of aroma composition(s).

Such an aroma composition comprises for the purposes of the present invention at least one volatile flavoring substance (this does not refer to compounds of Formula (I)). The at least one volatile flavoring substance here is preferably a sensorially active component with a vapor pressure of greater than or equal to 0.01 Pa at 25° C., preferably a vapor pressure of greater than or equal to 0.025 Pa at 25° C. Most volatile flavoring substances have a vapor pressure of greater than or equal to 1 Pa at 25° C. These flavoring substances are seen as particularly preferable for use in preparations, semi-finished products or flavoring mixtures according to the invention.

Examples of flavoring substances, that can be a component of the one of the abovementioned aroma compositions, can be found by way of example in K. Bauer, D. Garbe and H. Surburg, Common Fragrance and Flavor Materials, 4$^{th}$. Ed., Wiley-VCH, Weinheim 2001. The following are mentioned by way of example: organic acids (saturated and unsaturated) such as for example butanoic acid, acetic acid, methylbutanoic acid, caproic acid; alcohols (saturated and unsaturated) such as for example ethanol, propylene glycol, octenol, cis-3-hexenol, benzyl alcohol; sulfides and disulfides such as for example dimethylsulfide, difurfuryldisulfide, methylthiopropanal; thiols such as for example methylfuranthiol; pyrazines and pyrrolines such as for example methylpyrazine, acetylpyrazine, 2-propionylpyrroline, 2-acetylpyrroline; furan derivatives such as sotolon or 5-hydroxymethylfurfural.

The aroma compositions can also be used in the form of process flavorings (Maillard products) and/or extracts or essential oils of plants or plant parts of fractions thereof.

According to a further preferred embodiment of the present invention a preparation or semi-finished product according to the invention (as in each case described above) is in the form of a water-in-oil (W/O) emulsion.

Apart from the compound(s) to be used according to the invention of Formula (I) such an emulsion comprises water, an oily phase, one or a plurality of (consumable) W/O emulsifiers, optionally one or a plurality of antioxidants and optionally one or a plurality of substances for enhancing an antioxidative effect. Here with regard to preferred compounds of Formula (I) and mixtures of these that stated above applies by analogy.

The oily phase of such a W/O emulsion according to the invention consists of or comprises preferably a fatty oil and/or an aroma composition (preferably an aroma composition as described above).

Examples of fatty oils are, in particular, vegetable oils. Suitable fatty oils are for example, borage oil, thistle oil, peanut oil, hazelnut oil, coconut oil, pumpkin seed oil, linseed oil, corn oil, macadamia nut oil, almond oil, olive oil, palm kernel oil, pecan oil, pistachio oil, rapeseed oil, rice germ oil, sesame oil, soybean oil, sunflower oil, walnut oil or wheat germ oil, or fractions available from them. Liquid neutral esters based on medium chain fatty acids and glycerin, such as Miglyols (for example Miglyol 810, Miglyol 812), can also be used. Sunflower oil, palm kernel oil and rapeseed oil are preferred. Furthermore, fractionated coconut oils, which mainly comprise fatty acid residues having 6 through 8 C-atoms, are preferably used. These distinguish themselves by their taste neutrality and their good oxidation stability.

The consumable W/O emulsifier is preferably selected from the group consisting of lecithin (E 322), mono- and diglycerides of edible fatty acids (E 471), acetic acid monoglycerides (E 472a), lactic acid monoglycerides (E 472b), citric acid monoglycerides (E 472c), tartaric acid monoglycerides (E 472d), diacetyl tartaric acid monoglycerides (E 472e), and sorbitan monostearate (E 491).

Suitable antioxidants and substances, which can enhance the antioxidative effect, are in particular natural tocopherols and their derivates, tocotrienols, flavonoids, ascorbic acid and salts thereof, alpha-hydroxy acids (for example citric acid, lactic acid, malic acid, tartaric acid) and Na-, K- and Ca-salts thereof, ingredients isolated from plants, extracts or fractions thereof, for example, from tea, green tea, algae, grape seeds, wheat germs, rosemary, oregano, flavonoids, quercetin, phenolic benzyl amines. Also suitable as antioxidants are propyl gallate, octyl gallate, dodecyl gallate, butyl hydroxy anisole (BHA), butyl hydroxy toluene (BHT), lecithins, mono- and diglycerides of edible fatty acids esterified with citric acid, orthophosphates and Na-, K- and Ca-salts of monophosphoric acid and ascorbyl palmitate.

The W/O emulsions according to the invention are suitable particularly for applying to food surfaces, wherein the foodstuff preferably has a water content of up to 10 wt. %, preferably up to 5 wt. %. In a preferred embodiment, the W/O emulsion according to the invention has a sufficiently low viscosity at application temperature for this purpose, so that the application of the W/O emulsion by spraying is possible. Preferred foodstuffs, to whose surfaces an inventive W/O emulsion can be applied are, for example, crackers, chips (e.g. based on potatoes, corn, cereal or bread), extruded snack goods (e.g. flips) or leaching pastries (such as pretzel sticks). W/O emulsions according to the invention are normally applied to the foodstuff surfaces in an amount of 0.5 through 6 wt. % based on the total weight of the food.

Particularly preferably the compounds to be used according to the invention of Formula (I) or mixtures of these or flavoring mixtures according to the invention or vegetable extracts are used in monosodium glutamate-free or monosodium glutamate-reduced preparations or semi-finished products.

Consequently according to the invention monosodium glutamate-free preparations or semi-finished products or monosodium glutamate-reduced preparations or semi-finished products are particularly preferred.

Here the term "sodium glutamate-reduced" means that the preparation or semi-finished products according to the invention contain significantly less monosodium glutamate, than is contained in the normal preparation or semi-finished product; the monosodium glutamate content here is 5 through <100 wt. %, preferably 10 through 50 wt. %, particularly preferably 20 through 50 wt. % below the monosodium glutamate content of the normal preparation or semi-finished products. Where, in addition to one or a plurality of compounds of Formula (I), monosodium glutamate is also present in a preparation or semi-finished product according to the invention, the ratio of weight of the total quantity of compounds of Formula (I) to monosodium glutamate is preferably in the range 1:1 through 1:200.

As a result, particular preference is for those monosodium glutamate-reduced preparations or semi-finished products, wherein the ratio of weight of the total quantity of compounds of Formula (I) to the total quantity of monosodium glutamate, in relation to the dry weight of the preparation or semi-finished product, is in the range 1:1 through 1:200.

Particular preference is for those monosodium glutamate-reduced preparations (as described above), wherein
  the total quantity of monosodium glutamate is insufficient, in order in a comparative preparation, not comprising a compound of Formula (I), but otherwise with an identical composition (a normal monosodium glutamate-reduced preparation), to impart a (satisfactory) umami taste impression,
  and the total quantity of compounds of Formula (I) is sufficient, to impart to the preparation a (satisfactory) umami taste impression and optionally a (satisfactory) kokumi and/or a (satisfactory) salty taste impression.
The preparations and semi-finished products according to the invention for nutrition or pleasure are preferably selected from the group consisting of bakery products (for example bread, dry biscuits, cakes, other pastry products), beverages (for example vegetable juices, vegetable juice preparations), instant beverages (for example instant vegetable beverages), meat products (for example ham, fresh or cured sausage preparations, spiced or marinated fresh or cured meat products), spiced or marinated fish products (for example surimi), eggs or egg products (dried egg, egg white, egg yolk), cereal products (for example precooked ready rice products, rice flour products, millet and sorghum products, raw or precooked noodles and pasta products), dairy products (for example fresh cheese, soft cheese, hard cheese, milk drinks, whey, butter, partially or fully hydrolyzed milk protein-containing products), products made from soya protein or other soya bean fractions (for example soya milk and products made therefrom, soya lecithin-containing preparations, fermented products such as tofu or tempe or products made therefrom, soy sauces), vegetable preparations (for example ketchup, sauces, dried vegetables, deep-frozen vegetables, precooked vegetables, preserved vegetables, vegetable concentrates or pastes, cooked vegetables, potato preparations), snack articles (for example baked or fried potato chips or potato dough products, bread dough products, maize-, rice- or peanut-based extrudates), fat- or oil-based products or emulsions thereof (for example mayonnaise, spread, remoulade, dressings, condiments), other ready-to-serve meals and soups (for example dried soups, instant soups, precooked soups), sauces (instant sauces, dried sauces prepared sauces) spices or spice preparations (e.g. mustard preparations, horseradish preparations), spice mixtures and in particular powdered seasonings, which are for example used in snack food applications.

Monosodium glutamate-reduced or -free preparations and semi-finished products according to the invention for nutrition or pleasure are preferably selected from the group consisting of bakery products (for example bread, dry biscuits, cakes, other pastry products), vegetable preparations, meat products (for example ham, fresh or cured sausage preparations, spiced or marinated fresh or cured meat products), spiced or marinated fish products (for example surimi), eggs or egg products (dried egg, egg white, egg yolk), cereal products (for example precooked ready rice products, raw or precooked noodles and pasta products), dairy products (for example fresh cheese, soft cheese, hard cheese, milk drinks, whey, butter, partially or fully hydrolyzed milk protein-containing products), products made from soya protein or other soya bean fractions (for example soya milk and products made therefrom, soya lecithin-containing preparations, fermented products such as tofu or tempe or products made therefrom, soy sauces), fish sauces such as for example anchovy sauces, oyster sauces, vegetable preparations (for example ketchup, sauces, dried vegetables, deep-frozen vegetables, precooked vegetables, preserved vegetables, cooked vegetables, potato preparations), snack articles (for example baked or fried potato chips or potato dough products, bread dough product, maize-, or peanut-based extrudates), fat- or oil-based products or emulsions thereof (for example mayonnaise, spread, remoulade, dressings, condiments), ready-to-serve meals, soups (for example dried soups, instant soups, precooked soups), stock cubes, sauces (instant sauces, dried sauces prepared sauces), condiments, spices, spice preparations, spice mixtures and in particular powdered seasonings, which are for example used in snack food applications.

The preparations and semi-finished products according to the invention can also take the form of capsules, tablets (uncoated and coated tablets, for example coatings resistant to gastric juices), sugar-coated tablets, granules, pellets, mixtures of solids, dispersions in liquid phases, emulsions, powders, solutions, pastes or other swallowable or chewable preparations, for example as a food supplement.

The semi-finished products according to the invention as a rule are used to prepare ready-to-use or ready-to-serve preparations (according to the invention) for nutrition or pleasure.

In particular semi-finished products according to the invention can be used for further enhancement of the umami taste of monosodium glutamate-reduced foodstuffs and semi-luxury foods and also directly for the industrial or non-industrial preparation of foodstuffs or semi-luxury foods.

Particularly preferred according to the invention is a semi-finished product (as described above), which in relation to the total weight of the semi-finished product comprises a total quantity of monosodium glutamate in the range 0.00001 through 10 wt. %, preferably 0.0001 through 5 wt. %, particularly preferably 0.001 through 2 wt. %, or no monosodium glutamate.

Basically semi-finished products preferred according to the invention preferably contain:
  a total quantity of 1 ppm through 500 000 ppm, preferably 25 ppm through 100 000 ppm, in particular 50 ppm through 15 000 ppm of compounds of Formula (I),
  preferably a total quantity of 10 ppm through 100 000 ppm, preferably 25 ppm through 5 000 ppm, in particular 50 ppm through 1 200 ppm of compounds of Formula (I),
  no monosodium glutamate or a proportion of 0.00001 through 10 wt. %, preferably 0.0001 through 5 wt. %, in particular 0.001 wt. % through 2 wt. % of monosodium glutamate,
  and optionally a proportion of 0.0001 wt. % through 90 wt. %, preferably 0.001 wt. % through 30 wt. % of an aroma composition (preferably an aroma composition as described above),
in each case in relation to the total weight of the semi-finished products.

The preparations or semi-finished products according to the invention are preferably prepared by dissolving or mixing the compounds of Formula (I) in ethanol and if necessary demineralized and/or purified water. Then the solutions are converted by a drying process, preferably a spray-drying, vacuum freeze-drying, reverse osmosis, evaporation or other concentration process, or a combination of said process, into an (at least almost) solid form. Here the drying can take place with the help of carriers (e.g. starch, starch derivatives, maltodextrin, silica gel, etc., see above) or excipients (e.g. vegetable gums, stabilizers). The drying preferably takes place by means of spray-drying or vacuum freeze-drying.

Preferred preparations or semi-finished products according to the invention are spices, spice mixtures, seasonings, stock cubes, instant soups, instant sauces, vegetarian ready ready-to-serve meals, meat-containing ready-to-serve meals, fish sauces such as for example anchovy sauces, oyster sauces and soy sauces.

According to a further preferred embodiment for preparing the preparations or semi-finished products according to the invention, compounds of Formula (I) and optionally other components are firstly introduced into emulsions, into liposomes (e.g. based on phosphatidyl choline), into microspheres, into nanospheres or also into capsules, granules or extrudates from a matrix suitable for foodstuffs and semi-luxury foods (e.g. from starch, starch derivates, cellulose or cellulose derivates such as hydroxypropyl cellulose, other polysaccharides such as alginate, natural fats, natural waxes such as beeswax or carnauba wax or from proteins like gelatin).

In a further preferred preparation method compounds of Formula (I) are complexed with one or a plurality of suitable complexing agent(s), such as cyclodextrins or cyclodextrin derivates, preferably alpha- or betacyclodextrin, and used in this complex form.

Particularly preferred are preparations or semi-finished products according to the invention, in which the matrix is selected such that the compounds of Formula (I) have a delayed release from the matrix, so that a long-lasting effect is achieved. For the matrix, here for example natural fats, natural waxes (e.g. beeswax, carnauba wax) or also natural roughage (wheat fibers, apple fibers, oat fibers, orange fibers) can be used.

Further components of a ready-to-serve preparation for nutrition or pleasure according to the invention or a semi-finished product according to the invention can be normal basic materials, auxiliary materials and additives for foodstuffs or semi-luxury foods, e.g., water, mixtures of fresh or processed, vegetable or animal basic materials or raw materials (such as raw, fried, dried, fermented, smoked and/or cooked meat, bone, cartilage, fish, vegetables, herbs, nuts, vegetable juices or vegetable pastes or their mixtures), digestible or indigestible carbohydrate (e.g. sucrose, maltose, fructose, glucose, dextrins, amyloses, amylopectin, inulin, xylane, cellulose, tagatose), sugar alcohols (such as sorbitol, erythritol), natural or hardened fats (e.g. tallow, lard, palm oil, coconut oil, hardened vegetable fat), oils (such as sunflower oil, peanut oil, corn oil, olive oil, fish oil, soybean oil, sesame oil), fatty acids or their salts (e.g. potassium stearate), proteinogenic or non-proteinogenic amino acids and related compounds (e.g. gamma-aminobutyric acid, taurine), peptides (e.g., glutathione), native or processed proteins (such as gelatin), enzymes (e.g. peptidases), nucleic acids, nucleotides, taste modifiers for unpleasant taste impressions, other taste modulators for other, normally not unpleasant taste impressions, other taste-modulating substances (see also above; e.g. inositol phosphate, nucleotides such as guanosine monophosphate, adenosine monophosphate, or other substances such as monosodium glutamate or 2-phenoxypropionic acid), emulsifiers (for example, lecithins, diacylglycerols, gum Arabic), stabilizers (e.g., carrageenan, alginate), preservatives (such as benzoic acid and its salts, sorbic acid and its salts), antioxidants (such as tocopherol, ascorbic acid), chelating agents (such as citric acid), organic or inorganic acidifiers (such as acetic acid, phosphoric acid), additionally bitter substances (such as quinine, caffeine, limonin, amarogentin, humolone, lupolone, catechines, tannins), the enzymatic browning-prohibiting substances (e.g. sulfite, ascorbic acid), essential oils, plant extracts, natural or synthetic dyestuffs or pigments (such as carotenoids, flavonoids, anthocyans, chlorophyll and their derivates), spices, trigeminally effective substances or plant extracts containing such trigeminally effective substances, synthetic, natural or natural-identical flavorings or odorous substances and odor modifiers.

Preferably preparations or semi-finished products according to the invention also contain an aroma composition (as described above), in order to round-off and refine the taste and/or smell.

Suitable aroma compositions preferably contain synthetic, natural or natural-identical aroma, aromatic and flavoring substances, process flavorings, smoke flavorings or other aroma-providing preparations (e.g. protein [partial-] hydrolyzates, barbecue flavors, plant extracts, spices, spice preparations, vegetables and/or vegetable preparations), and optionally suitable excipients and carrier substances. In particular here flavoring components or their ingredients are suitable which create a roast, meaty (in particular chicken, fish, marine animals, beef, pork, lamb, sheep, goat), vegetarian (in particular tomato, onion, garlic, celery, leek, mushrooms, eggplant, seaweed), a savory (in particular black and white pepper, chili, paprika, pepper, cardamom, nutmeg, allspice, mustard and mustard products), fried, yeasty, boiled, greasy, salty and/or hot flavor impression, and thus can advantageously enhance the savory impression. As a rule, the flavoring compositions contain more than one of said ingredients.

Particularly preferably a flavoring mixture according to the invention, preparation according to the invention or semi-finished product according to the invention additionally comprises one or a plurality of substances not corresponding to Formula (I) to mask or reduce an unpleasant, in particular a bitter, metallic, chalky, acidic and/or astringent taste, and/or one or a plurality of substances not corresponding to Formula (I) for imparting or enhancing a pleasant taste impression, in particular a sweet or salty taste impression, a kokumi taste impression or an umami taste impression.

According to a further aspect of the present invention a flavoring mixture according to the invention, preparation according to the invention or semi-finished product according to the invention (additionally) comprises one or a plurality of flavorings not corresponding to Formula (I), that impart a non-tangy and/or non-warming stimulation, in particular a stimulation selected from the group consisting of tingling, prickling, piercing, cooling and astringent, wherein the flavoring not corresponding to Formula (I) or one, a plurality of or all the flavorings not corresponding to Formula (I) is or are preferably selected from the group consisting of hesperetin, phloretin, cis-pellitorin and trans-pellitorin.

Particularly preferred is a cis- and/or trans-pellitorin-containing flavoring mixture, preparation or semi-finished product according to the invention, wherein the total quantity of pellitorin in relation to the total weight of the flavoring mixture, the preparation or the semi-finished product is preferably in the range 0.5 through 500 ppm, preferably in the range 5 through 100 ppm.

Thus for example by combining the compounds to be used according to the invention of Formula (I) with hesperetin and/or phloretin on the one hand and cis- and/or trans-pellitorin (see WO 2004/000787 or WO 2004/043906) on the other, a further improved taste profile, that is also preferred by consumers, can be achieved.

Modulating aroma and flavoring substances are preferably selected from the group consisting of adenosine 5'-monophosphate, cytidine 5'-monophosphate, inosin-5'-monophosphate, and the pharmaceutically acceptable salts thereof; lactisoles; 2,4-dihydroxybenzoic acid; 3-hydroxybenzoic acid; sodium salts, preferably sodium chloride, sodium lactate, sodium citrate, sodium acetate, sodium gluconoate; hydroxyflavanones, such as for example eriodictyol, homoeriodictyol, and the sodium salts thereof; hydroxybenzoic acid amides, such as for example 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxybenzyl)amide, 2-hydroxybenzoic acid N-4-(hydroxy-3-methoxybenzyl)amide, 4-hydroxybenzoic acid N-(4-hydroxy-3-methoxybenzyl)amide, 2,4-dihydroxybenzoic acid N-(4-hydroxy-3-methoxybenzyl)amide monosodium salt, 2,4-dihydroxybenzoic acid N-2-(4-hydroxy-3-methoxyphenyl)ethylamide, 2,4-dihydroxybenzoic acid N-(4-hydroxy-3-ethoxybenzyl)amide, 2,4-dihydroxybenzoic acid N-(3,4-dihydroxybenzyl)amide and 2-hydroxy-5-methoxy-N-[2-(4-hydroxy-3-methoxyphenyl)ethylamide, 4-hydroxybenzoic acid vanillylamide (in particular those described in WO 2006/024587, which as regards the corresponding compounds disclosed therein, is incorporated into the present application for reference); hydroxydeoxybenzoins, such as for example 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)-ethanone, 1-(2-hydroxy-4-methoxyphenyl)-2-(4-hydroxy-3-methoxyphenyl)ethanone (in particular those described in WO 2006/106023 and DE 10 2009 002268.6, which as regards the corresponding compounds disclosed therein, are incorporated into the present application for reference); hydroxyphenyl alkane diones, such as gingerdion-[2], gingerdion-[3], gingerdion-[4], dehydrogingerdion-[2], dehydrogingerdion-[3], dehydrogingerdion-[4]) (in particular those as described in WO 2007/003527, which as regards the corresponding compounds disclosed therein, is incorporated into the present application for reference); diacetyl trimers (in particular those as described in WO 2006/058893 which as regards the corresponding compounds disclosed therein, is incorporated into the present application for reference); gamma-aminobutyric acids (in particular those as described in WO 2005/096841 which as regards the corresponding compounds disclosed therein, is incorporated into the present application for reference) and divanillins (in particular those described in WO 2004/078302 which as regards the corresponding compounds disclosed therein, is incorporated into the present application for reference); bicyclo[4.1.0]heptane-7-carboxylic acid amides, in particular those described in PCT/EP2007/061171 and the documents based thereon (Symrise), which as regards the corresponding compounds disclosed therein, are incorporated into the present application for reference; cyclopropanecarboxylic acid (3-methylcyclohexyl)amide, in particular those described described in U.S. Provisional application 60/916,589 of May 5, 2007 and the documents based thereon (Symrise), which as regards the corresponding compounds disclosed therein, are incorporated into the present application for reference; aromatic neomenthyl amides, in particular those described in US-Provisional Application 60/984,023 of Oct. 31, 2007 and the documents based thereon (Symrise), which as regards the corresponding compounds disclosed therein, is incorporated into the present application for reference; geranylamine derivates of oxalic acid, in particular those described in EP 2168442 and the documents based thereon (Symrise), which as regards the corresponding compounds disclosed therein, are incorporated into the present application for reference; neomenthyl derivates as described in US 2009 0311401-A1 and the patent documents based thereon (Symrise), which as regards the corresponding compounds disclosed therein, is incorporated into the present application for reference.

In connection with the present invention a method is also described for imparting, modifying and/or enhancing an umami, kokumi and/or salty taste of a ready-to-use or ready-to-serve preparation or semi-finished product for nutrition or pleasure. Such a method comprises the following step

- mixing of an umami-tasting effective quantity (for preferred quantities see above), of one or a plurality of compounds of Formula (I) to be used according to the invention or a flavoring mixture (as described above) according to the invention or vegetable extract according to the invention (as described above) with one or a plurality of further components of the preparation or semi-finished products, or
- applying an umami-tasting effective quantity of one or a plurality of compounds of Formula (I) or flavoring mixture according to the invention or a vegetable extract according to the invention (as in each case described above) to one or a plurality of further components of the preparation or semi-finished product, or
- embedding an effective amount for taste purposes of one or a plurality of compounds of Formula (I) or a flavoring mixture according to the invention or a vegetable extract according to the invention (as in each case described above) in a shell or matrix material.

Here, with regard to the preferred compounds of Formula (I) or components and quantities that stated above applies by analogy.

Further aspects of the present invention can be inferred from the following examples and the attached claims.

EXAMPLES

The examples serve to clarify the invention without restricting it. Unless otherwise stated, all details refer to the weight.

Example 1

Simple Profiling of Example Cinnamides (Compounds (1), (3) and (9))

The compounds were dissolved in water in the stated concentration and assessed by a group of experts by tasting with open discussion.

| Structure | Name (compound number) | Taste profile (concentration in mg/kg) |
|---|---|---|
| [structure image] | Rubemamine (1) | Umami (10 mg/kg) |
| [structure image] | Rubesconamine (3) | Umami, otherwise neutral (10 mg/kg) |

-continued

| Structure | Name (compound number) | Taste profile (concentration in mg/kg) |
|---|---|---|
| (structure shown) | Zanthomamine (9) | Somewhat delayed onset of umami effect (50 mg/kg) |

Example 2

Profiling of Example Cinnamides (Compounds (1) and (3)) in a Complex Base

An American beef extract as the base, a corresponding base mixed with monosodium glutamate and a corresponding base mixed with the cinnamide were in each case administered blind individually to 15-25 trained panelists for profiling. Using the descriptors previously decided upon by discussion (mouth-fill, salty, metallic, meaty, bitter, mouth-watering, barbecued-roasted, sweet, sour, lingering) the strength of these was assessed on a scale of 0 (imperceptible) through 9 (very strong). The individual results of the panelists were averaged.

In the spider chart attached as FIG. 1 the profile of an American beef extract as the base (i) is compared with such a base with the addition of 10 ppm (iii) or 50 ppm rubemamine (compound (3)) (iv) and with a sample (ii) of such a base with the addition of 0.05 wt. % MSG (monosodium glutamate).

In the spider chart attached as FIG. 2 the profile of an American beef extract as the base (i) is compared with such a base with the addition of 5 ppm (iii) or 10 ppm rubemamine (compound (3)) (iv) and with a sample (ii) of such a base with the addition of 0.05 wt. % MSG (monosodium glutamate).

Example 3

Profiling of Example Cinnamides (Compounds (1), (3) and (9)) in a Complex Base Together with Monosodium Glutamate (Enhancing Effect)

An American beef extract as the base, a corresponding sauce mixed with monosodium glutamate, a corresponding sauce mixed with the cinnamide and a corresponding base mixed with monosodium glutamate were in each case administered blind individually to 15-25 trained panelists for profiling. Using the descriptors previously decided upon by discussion (mouth-fill, salty, metallic, meaty, bitter, mouth-watering, barbecued-roasted, sweet, sour, lingering) the strength of these was assessed on a scale of 0 (imperceptible) through 9 (very strong). The individual results of the panelists were averaged.

Evidence of the enhancement of the monosodium glutamate effect is provided by the spider chart attached as FIG. 3. Here (i) the beef extract as the base is compared with (ii) such a base with the addition of 0.05% monosodium glutamate, (iii) such as base with the addition of 0.0025% monosodium glutamate and (iv) such a base with the addition of 0.0025% monosodium glutamate and 20 ppm rubemamine (1). While the sample (iii) overall for the parameters investigated was perceived as less strong than the sample (i) without the addition, the high glutamate content sample (ii) and the sample with the low concentration of glutamate and rubemamine (iv)—except for slightly less sweetness were virtually indistinguishable.

Rubescenamine (compound (3)) in particular is advantageously also suitable in particularly low concentration for enhancing the monosodium glutamate effect, as is demonstrated by the spider chart attached as FIG. 4. Here again (i) a beef extract as the base is compared with (ii) such a base with the addition of 0.05% monosodium glutamate, (iii) such a base with the addition of 0.0025% monosodium glutamate and (iv) such a base with the addition of 0.0025% monosodium glutamate and 5 ppm rubescenamine (3). Here also the sample with the low concentrate of glutamate and rubescenamine (iv) was assessed more strongly on virtually all parameters than sample (iii) and in particular for the "salty" parameter was assessed similarly to sample (ii).

Zanthomamine (compound (9)) in particular is likewise particularly suited to enhancing the monosodium glutamate effect, as evidenced by the spider diagram attached as FIG. 5. Here again (i) a beef extract as the base is compared with (ii) such a base with the addition of 0.05% monosodium glutamate, (iii) such a base with the addition of 0.0025% monosodium glutamate and (iv) such a base with the addition of 0.0025% monosodium glutamate and with the addition of 50 ppm zanthomamine (9). Here also the sample with the low concentration of glutamate and zanthomamine (iv) was assessed more strongly on virtually all parameters than sample (iii).

Application Examples

The application examples serve to clarify the invention without restricting it. Unless otherwise state, all details refer to the weight.

Application Example 1

Spray-Dried Compositions

|  | Component | Amount |
|---|---|---|
| 1.1 | Rubemamine (1) | 10 g |
|  | Maltodextrin | 90 g |
| 1.2 | Rubescenamine(3) | 10 g |
|  | Maltodextrin | 90 g |

The components are dissolved in a mixture of ethanol and demineralized water and then spray-dried. The compositions are used in the following application examples.

Application Example 2

Aroma Composition, not According to the Invention

| Ingredient | Amount |
| --- | --- |
| 10 wt. % trans-pellitorin in 1,2-propylene glycol/diethylmalonate | 0.25 g |
| Hesperetin | 2.50 g |
| Phloretin | 1.50 g |
| Propylene glycol | 95.75 g |

The aroma composition is used in the application examples described below.

Application Example 3

Condiment

| Part | Component | Amount |
| --- | --- | --- |
| A | Rubemamine (1) | 0.2 g |
|   | Sodium chloride | 15 g |
| B | Mustard powder | 5 g |
|   | Mustard flavoring | 0.1 g |

Part A is weighed-in. 290 ml water are provided then mixed with part A and dissolved while stirring. The solution is diluted with water to 1.84 kg (pH 6.0) and then freeze-dried (eutectic point: −15° C.; working vacuum: 0.52 mbar; shelf temperature: −5° C. through +25° C.). The product is mixed with mustard powder and the mustard flavoring from part B and packed as a condiment.

Application Example 4

Process Flavoring

|  | Usage [g] | | | |
| --- | --- | --- | --- | --- |
| Ingredient | Version A | Version B | Version C | Version D |
| L-alanine | 41.0 | 41.0 | 41.0 | 41.0 |
| L-aspartic acid | 123.0 | 123.0 | 123.0 | 123.0 |
| Succinic acid | 4.7 | 4.7 | 4.7 | 4.7 |
| Calcium chloride dihydrate | 7.0 | 7.0 | 7.0 | 7.0 |
| L-cysteine•HCl monohydrate | 11.0 | 11.0 | 11.0 | 11.0 |
| Dipotassium phosphate | 6.0 | 6.0 | 6.0 | 6.0 |
| Powdered fructose | 1.0 | 1.0 | 1.0 | 1.0 |
| L-isoleucine | 1.6 | 1.6 | 1.6 | 1.6 |
| Potassium chloride | 228.0 | 228.0 | 228.0 | 228.0 |
| L-leucine | 1.6 | 1.6 | 1.6 | 1.6 |
| L-lysine•HCl | 3.6 | 3.6 | 3.6 | 3.6 |
| Magnesium chloride hexahydrate | 19.0 | 19.0 | 19.0 | 19.0 |
| Maltodextrin | 49.0 | 49.0 | 49.0 | 49.0 |
| L-phenylalanine | 2.0 | 2.0 | 2.0 | 2.0 |
| L-proline | 74.0 | 74.0 | 74.0 | 74.0 |
| L-serin | 6.5 | 6.5 | 6.5 | 6.5 |
| L-threonine | 3.0 | 3.0 | 3.0 | 3.0 |
| L-valine | 9.0 | 9.0 | 9.0 | 9.0 |
| Water | 384.0 | 389.0 | 379.0 | 379.0 |
| Rubemamine (1) | 25.0 | 0 | 20 | 0 |
| Rubescenamine (3) | 0 | 20 | 10 | 0 |
| Zanthomamine (9) | 0 | 0 | 0 | 30 |

All components are mixed at 40° C. and then heated at 85° C. for 10 minutes (reflux reaction). After cooling to 40° C. the pH is adjusted to 5 with potassium hydroxide solution. These "umami" process flavorings can be worked into bouillon—preparations C or D of application example 9 in place of the pure compounds of Formula (I), wherein it is preferable in preparation C to use 5 g and in preparation D 13 g of the "umami" process flavoring.

Application Example 5

Instant Soup, Cream of Leek Type

| Component | A | B | C | D | E |
| --- | --- | --- | --- | --- | --- |
| Potato starch | 20.0 g | 20.0 g | 20.0 g | 20.0 g | 20.0 g |
| Fat powder | 25.0 g | 25.0 g | 25.0 g | 25.0 g | 25.0 g |

-continued

| Component | A | B | C | D | E |
|---|---|---|---|---|---|
| Lactose | 20.0 g | 20.0 g | 20.0 g | 20.0 g | 20.0 g |
| Maltodextrin | 11.730 g | 14.714 g | 14.710 g | 14.680 g | 15.705 g |
| Table salt | 8.0 g | 8.0 g | 8.0 g | 8.0 g | 7.0 g |
| Monosodium glutamate | 3.0 g | — | — | — | — |
| Spinach powder | 2.0 g | 2.0 g | 2.0 g | 2.0 g | 2.0 g |
| Green leek powder | 2.0 g | 2.0 g | 2.0 g | 2.0 g | 2.0 g |
| Citric acid in powder form | 0.3 g | 0.3 g | 0.3 g | 0.3 g | 0.3 g |
| Hardened vegetable fat | 3.0 g | 3.0 g | 3.0 g | 3.0 g | 3.0 g |
| Freeze-dried leek | 1.0 g | 1.0 g | 1.0 g | 1.0 g | 1.0 g |
| Chicken flavoring | 1.0 g | 1.0 g | 1.0 g | 1.0 g | 1.0 g |
| "Green leek" type seasoning, powder | 2.0 g | 2.0 g | 2.0 g | 2.0 g | 2.0 g |
| "Fried onions" type seasoning, | 0.6 g | 0.6 g | 0.6 g | 0.6 g | 0.6 g |
| Yeast seasoning, "Vegetable broth" type, powder | 0.3 g | 0.3 g | 0.3 g | 0.3 g | 0.3 g |
| Curcuma extract | 0.07 g | 0.07 g | 0.07 g | 0.07 g | 0.07 g |
| Rubemamine (1) | — | 0.0025 g | — | 0.050 g | 0.015 g |
| Rubescenamine (3) | — | — | 0.0025 g | — | 0.010 g |

A = Comparative preparation
B, C, D = Preparations according to the invention (monosodium glutamate-free)
E = Preparations according to the invention (reduced salt and monosodium glutamate-free)

5 g of the respective powder mixture in each case have 100 ml of hot water poured onto them, in order to obtain a ready-to-serve soup.

Application Example 6

Instant Soup, Chicken Noodle Type

| Component | A | B | C | D | E |
|---|---|---|---|---|---|
| Starch | 16.0 g | 16.0 g | 16.0 g | 16.0 g | 16.0 g |
| Table salt | 7 g | 7 g | 7 g | 7 g | 5 g |
| Sucrose, refined | 3.2 g | 3.2 g | 3.2 g | 3.2 g | 3.2 g |
| Monosodium glutamate | 3.2 g | — | — | — | — |
| Sodium inosinate/sodium guanylate in a ratio of 1:1 | 0.8 g | 0.8 g | 0.8 g | 0.8 g | 0.8 g |
| Acid hydrolyzed vegetable protein | 8.0 g | 8.0 g | 8.0 g | 8.0 g | 8.0 g |
| Fat powder | 2.0 g | 2.0 g | 2.0 g | 2.0 g | 2.0 g |
| Vegetable fat, spray-dried | 1.0 g | 1.0 g | 1.0 g | 1.0 g | 1.0 g |
| Freeze-dried diced chicken | 2.0 g | 2.0 g | 2.0 g | 2.0 g | 2.0 g |
| Soup noodle | 32.0 g | 32.0 g | 32.0 g | 32.0 g | 32.0 g |
| Maltodextrin | 12.160 g | 15.339 g | 14.135 g | 14.110 g | 15.144 g |
| Freeze-dried Chinese vegetables | 4.6 g | 4.6 g | 4.6 g | 4.6 g | 4.6 g |
| Chicken flavoring | 8.0 g | 8.0 g | 8.0 g | 8.0 g | 8.0 g |
| Riboflavin food coloring | 0.04 g | 0.04 g | 0.04 g | 0.04 g | 0.04 g |
| Rubemamine (1) | — | 0.0025 g | 0.025 g | 0.05 g | 0.015 g |
| Flavor composition according to application example 2 | — | — | 1.2 g | 1.2 g | 1.2 g |

A = Comparative preparation
B, C, D = Preparations according to the invention (monosodium glutamate-free)
E = Preparations according to the invention (reduced salt and monosodium glutamate-free)

4.6 g of the respective powder mixture are boiled for 10 minutes in 100 ml of water in each case in order to obtain a ready-to-serve soup.

Application Example 7

"Pepper" Type Seasoning

| Component | A | B | C | D | E |
|---|---|---|---|---|---|
| Milk protein | 0.8 g | 0.8 g | 0.8 g | 0.8 g | 0.8 g |
| Carob gum | 2.0 g | 2.0 g | 2.0 g | 2.0 g | 2.0 g |
| Corn starch | 22.0 g | 27.995 g | 27.965 g | 27.340 g | 29.900 g |
| Table salt | 14.0 g | 14.0 g | 14.0 g | 14.0 g | 12.0 g |
| Paprika powder | 13.0 g | 13.0 g | 13.0 g | 13.0 g | 13.0 g |
| Tomato powder | 13.0 g | 13.0 g | 13.0 g | 13.0 g | 13.0 g |
| Sucrose | 4.0 g | 4.0 g | 4.0 g | 4.0 g | 4.0 g |
| Garlic powder | 0.5 g | 0.5 g | 0.5 g | 0.5 g | 0.5 g |
| Hardened vegetable fat | 8.0 g | 8.0 g | 8.0 g | 8.0 g | 8.0 g |

-continued

| Component | A | B | C | D | E |
|---|---|---|---|---|---|
| Fat powder | 11.0 g | 11.0 g | 11.0 g | 11.0 g | 11.0 g |
| Monosodium glutamate | 6.0 g | — | — | — | — |
| Food coloring beetroot and paprika | 2.0 g | 2.0 g | 2.0 g | 2.0 g | 2.0 g |
| "Pepper" type flavoring | 2.0 g | 2.0 g | 2.0 g | 2.0 g | 2.0 g |
| "Pizza" type flavoring | 1.2 g | 1.2 g | 1.2 g | 1.2 g | 1.2 g |
| "Tomato" type flavoring | 0.4 g | 0.4 g | 0.4 g | 0.4 g | 0.4 g |
| Black pepper extract | 0.1 g | 0.1 g | 0.1 g | 0.1 g | 0.1 g |
| Rubemamine (1) | — | 0.005 g | — | 0.060 g | 0.10 g |
| Rubescenamine(3) | — | — | 0.035 g | 0.060 g | — |

A = Comparative preparation
B, C, D = Preparations according to the invention (sodium glutamate-free)
E = Preparations according to the invention (reduced salt and monosodium glutamate-free)

100 g of pork neck steak at a time are evenly sprinkled with 1.7 g of preparations A, B, C and D respectively and then fried.

Application Example 8

Tomato Ketchup

| Component | A | B | C | D |
|---|---|---|---|---|
| Monosodium glutamate | 0.40 g | — | — | — |
| Table salt | 2 g | 1 g | 2 g | 1 g |
| Starch, Farinex WM 55 | 1 g | 1 g | 1 g | 1 g |
| Sucrose | 12 g | 9.2 g | 9.2 g | 9.2 g |
| Double strength tomato concentrate | 40 g | 40 g | 40 g | 40 g |
| Glucose syrup 80 Brix | 18 g | 18 g | 18 g | 18 g |
| Brandy vinegar 10% | 7 g | 7 g | 7 g | 7 g |
| Water | 19.60 g | 23.80 g | 22.30 g | 23.25 g |
| Flavor composition according to application example 2.1 | — | — | 0.4 g | 0.4 g |
| 5% solution of rubemamine (1) in propylene glycol | — | — | 0.10 g | — |
| 5% solution of rubescenamine(3) in propylene glycol | — | — | — | 0.15 g |

A = Comparative preparation
B = Comparative preparation (reduced salt and sugar, monosodium glutamate-free)
C = Preparation according to the invention (monosodium glutamate-free, reduced sugar)
D = Preparation according to the invention (reduced salt and sugar, monosodium glutamate-free)

The ingredients are mixed in the order stated and the finished ketchup is homogenized using a stirrer, filled in bottles and sterilized.

Application Example 9

Bouillon

| Component | A | B | C | D | E |
|---|---|---|---|---|---|
| Fat powder | 8.77 g | 8.77 g | 8.77 g | 8.77 g | 8.77 g |
| Monosodium glutamate | 8.77 g | 5 g | 5 g | — | — |
| Powdered yeast extract | 12.28 g | 12.28 g | 12.28 g | 12.28 g | 12.28 g |
| Table salt | 29.83 g | 29.83 g | 29.83 g | 29.83 g | 26.83 g |
| Maltodextrin | 37.28 g | 41.050 g | 41.040 g | 45.090 g | 48.950 g |
| Natural vegetable extract | 3.07 g | 3.07 g | 3.07 g | 3.07 g | 3.07 g |
| Rubemamine (1) | — | — | 0.010 g | 0.030 g | — |
| Rubescenamine(3) | — | — | — | 0.030 g | 0.100 g |

A = Comparative preparation
B = Comparative preparation (monosodium glutamate-reduced)
C = Preparation according to the invention
D = Preparation according to the invention (monosodium glutamate-free)
E = Preparation according to the invention (reduced salt and monosodium glutamate-free)

1 000 ml of hot water are poured onto 15 g each of the respective powder mixtures.

Application Example 10

Seasoning for Potato Chips

| Component | A | B | C | D | E |
|---|---|---|---|---|---|
| Monosodium glutamate | 3.50 g | 2.00 g | 2.00 g | — | 1.00 g |
| Cheese powder | 10.00 g | 10.00 g | 10.00 g | 10.00 g | 10.00 g |
| Garlic powder | 2.00 g | 2.00 g | 2.00 g | 2.00 g | 2.00 g |
| Whey powder | 38.86 g | 40.36 g | 40.06 g | 41.91 g | 44.76 g |
| Spice extract oil | 0.20 g | 0.20 g | 0.20 g | 0.20 g | 0.20 g |
| Paprika powder | 9.80 g | 9.80 g | 9.80 g | 9.80 g | 9.80 g |
| Table salt | 21.00 g | 21.00 g | 21.00 g | 21.00 g | 17.00 g |
| Tomato powder | 9.00 g | 9.00 g | 9.00 g | 9.00 g | 9.00 g |
| Dry flavoring | 2.50 g | 2.50 g | 2.50 g | 2.50 g | 2.50 g |
| Silicon dioxide | 0.02 g | 0.02 g | 0.02 g | 0.02 g | 0.02 g |
| Vegetable oil | 0.02 g | 0.02 g | 0.02 g | 0.02 g | 0.02 g |
| Onion powder | 3.00 g | 3.00 g | 3.00 g | 3.00 g | 3.00 g |
| Concentrated cream flavoring | 0.03 g | 0.03 g | 0.03 g | 0.03 g | 0.03 g |
| Cheese flavoring | 0.03 g | 0.03 g | 0.03 g | 0.03 g | 0.03 g |
| Concentrated tomato flavoring | 0.04 g | 0.04 g | 0.04 g | 0.04 g | 0.04 g |
| Spray-dried composition according to Example 1.1 | — | — | 0.30 g | — | 0.30 g |
| Spray-dried composition according to Example 1.2 | — | — | — | 0.45 g | 0.30 g |

A = Comparative preparation
B = Comparative preparation (monosodium glutamate-reduced)
C = Preparation according to the invention (monosodium glutamate-reduced)
D = Preparation according to the invention (monosodium glutamate-free)
E = Preparation according to the invention (monosodium glutamate-reduced and reduced salt)

6 g of the seasoning are spread over 94 g potato chips.

Application Example 11

White Sauce

| Component | A | B | C | D | E |
|---|---|---|---|---|---|
| Maltodextrin | 25.98 g | 27.18 g | 27.08 g | 27.58 g | 28.43 g |
| Table salt | 7.50 g | 7.50 g | 7.50 g | 7.50 g | 6.00 g |
| Monosodium glutamate | 2.00 g | 0.80 g | 0.80 g | — | 0.80 g |
| Vegetable fat | 5.00 g | 5.00 g | 5.00 g | 5.00 g | 5.00 g |
| Pepper, white | 0.02 g | 0.02 g | 0.02 g | 0.02 g | 0.02 g |
| Onion powder | 1.50 g | 1.50 g | 1.50 g | 1.50 g | 1.50 g |
| Pregelatinized corn starch | 30.00 g | 30.00 g | 30.00 g | 30.00 g | 30.00 g |
| Fat powder | 28.00 g | 28.00 g | 28.00 g | 28.00 g | 28.00 g |
| Spray-dried composition according to Example 1.1 | — | — | 0.10 g | — | 0.20 g |
| Spray-dried composition according to Example 1.2 | — | — | — | 0.40 g | 0.05 g |

A = Comparative preparation
B = Comparative preparation (monosodium glutamate-reduced)
C = Preparation according to the invention (monosodium glutamate-reduced)
D = Preparation according to the invention (monosodium glutamate-free)
E = Preparation according to the invention (monosodium glutamate-reduced and reduced salt)

1 000 ml of hot water are poured onto 90 g of the sauce mixture and stirred vigorously with the whisk.

Application Example 12

Brown Sauce

| Component | A | B | C | D | E |
|---|---|---|---|---|---|
| Starch | 40.00 g | 40.00 g | 40.00 g | 40.00 g | 40.00 g |
| Maltodextrin | 33.10 g | 33.80 g | 33.66 g | 34.70 g | 35.07 g |
| Table salt | 6.00 g | 6.00 g | 6.00 g | 6.00 g | 4.50 g |
| Spirit caramel, spray-dried | 5.00 g | 5.00 g | 5.00 g | 5.00 g | 5.00 g |
| Yeast extract powder | 3.00 g | 3.00 g | 3.00 g | 3.00 g | 3.00 g |
| Monosodium glutamate | 2.00 g | 1.30 g | 1.30 g | — | 1.30 g |
| Sugar | 0.50 g | 0.50 g | 0.50 g | 0.50 g | 0.50 g |
| Fat powder | 5.00 g | 5.00 g | 5.00 g | 5.00 g | 5.00 g |
| Tomato powder | 3.00 g | 3.00 g | 3.00 g | 3.00 g | 3.00 g |
| Natural vegetable extract | 1.00 g | 1.00 g | 1.00 g | 1.00 g | 1.00 g |
| Onion extract | 0.30 g | 0.30 g | 0.30 g | 0.30 g | 0.30 g |
| Pepper extract | 0.10 g | 0.10 g | 0.10 g | 0.10 g | 0.10 g |
| Dry flavoring | 1.00 g | 1.00 g | 1.00 g | 1.00 g | 1.00 g |
| Spray-dried composition according to Example 1.2 | — | — | 0.70 g | 2.00 g | 0.70 g |

A = Comparative preparation

B = Comparative preparation (monosodium glutamate-reduced)

C = Preparation according to the invention (monosodium glutamate-reduced)

D = Preparation according to the invention (monosodium glutamate-free)

E = Preparation according to the invention (monosodium glutamate-reduced and reduced salt)

1 000 ml of hot water are poured onto 90 g of the sauce mixture and stirred vigorously with the whisk.

Application Example 13

Tomato Soup

| Component | A | B | C | D | E |
|---|---|---|---|---|---|
| Water | 50.65 g | 50.80 g | 50.799 g | 51.035 g | 51.29 g |
| Vegetable oil | 5.50 g | 5.50 g | 5.50 g | 5.50 g | 5.50 g |
| Tomato paste | 24.00 g | 24.00 g | 24.00 g | 24.00 g | 24.00 g |
| Cream | 1.05 g | 1.05 g | 1.05 g | 1.05 g | 1.05 g |
| Sugar | 2.00 g | 2.00 g | 2.00 g | 2.00 g | 2.00 g |
| Table salt | 1.70 g | 1.70 g | 1.70 g | 1.70 g | 1.20 g |
| Monosodium glutamate | 0.40 g | 0.25 g | 0.25 g | — | 0.25 g |
| Wheat flour | 5.50 g | 5.50 g | 5.50 g | 5.50 g | 5.50 g |
| Starch | 1.20 g | 1.20 g | 1.20 g | 1.20 g | 1.20 g |
| Diced tomatoes | 8.00 g | 8.00 g | 8.00 g | 8.00 g | 8.00 g |
| Spray-dried composition according to Example 1.1 | — | — | 0.001 g | 0.015 g | 0.010 g |

A = Comparative preparation

B = Comparative preparation (monosodium glutamate-reduced)

C = Preparation according to the invention (monosodium glutamate-reduced)

D = Preparation according to the invention (monosodium glutamate-free)

E = Preparation according to the invention (monosodium glutamate-reduced and reduced salt)

The solid components are weighed-in and mixed and then the water is added. The vegetable oil is gradually added followed by the tomato paste. The mixture is boiled up while stirring.

Application Example 14

Application in a Green Tea Drink

| Ingredient | Usage in wt. % | |
| --- | --- | --- |
| | Version A | Version B |
| Green tea concentrate | 18.00 | 18.00 |
| 5% solution of rubemamine (1) propylene glycol | 0.002 | — |
| 5% solution of rubescenamine (3) propylene glycol | — | 0.002 |
| Demineralized water | 81.998 | 81.998 |

The green tea concentrate is mixed with the respective 5% solution of the cinnamide to be used according to the invention of Formula (I) in propylene glycol. Then the volume is made up with demineralized water followed by further thorough mixing. The product is then filtered, packed ready for use and sterilized at 118° C.

Application Example 15

Meat Seasoning for (Ready-Prepared) Pasta

| Ingredient | wt. % |
| --- | --- |
| Meat flavoring | 5 |
| Caramel | 3.00 |
| Citric acid (anhydrous) | 0.40 |
| Chives (drained) | 2.00 |
| Maltodextrin (from tapioca) | 10.30 |
| Monosodium glutamate | 15.00 |
| Onion powder | 5.00 |
| Ribotide | 0.80 |
| Sodium chloride | 45.65 |
| Sugar | 2.80 |
| Sweet whey powder | 6.50 |
| 10% solution of rubemamine (1) in propylene glycol | 0.05 |

All ingredients are blended resulting in a homogenous mixtures.

Application Example 17

(Ready Prepared) Pasta

| Part | Ingredient | wt. % |
| --- | --- | --- |
| A | Wheat flour | 62.00 |
| | Potato starch | 10.90 |
| B | Salt | 1.10 |
| | Guargum | 0.06 |
| | Sodium carbonate | 0.07 |
| | Potassium carbonate | 0.25 |
| | $Na_2H_2P_2O_7$ | 0.07 |
| | 10% solution of rubescenamine (3) in propylene glycol | 0.05 |
| C | Water | 25.45 |

A suspension of ingredients B in water is added to a mixture of ingredients A and kneaded into a dough. After the dough has rested for approximately 5 minutes, this is processed into sheets with a pasta machine, and in a final stage is cut to the normal shape. After 3 minutes' cooking time the pasta is ready to eat and can, for example, be served with 8 g of the meat seasoning (application example 16).

The taste of a 0.5% American beef extract as base (i) was compared in a tasting by a panel of trained test subjects with the taste of such a base with 10 ppm (iii) or 50 ppm (iv) rubemamine (1) added, and such a base with 0.05 wt. % MSG added (ii).

The test subjects assessed the strength of the stated flavors by giving a score on a scale of 0 (imperceptible) through 9 (very strong corresponding taste). The mean values of the respective scorings are shown.

Figure 1:
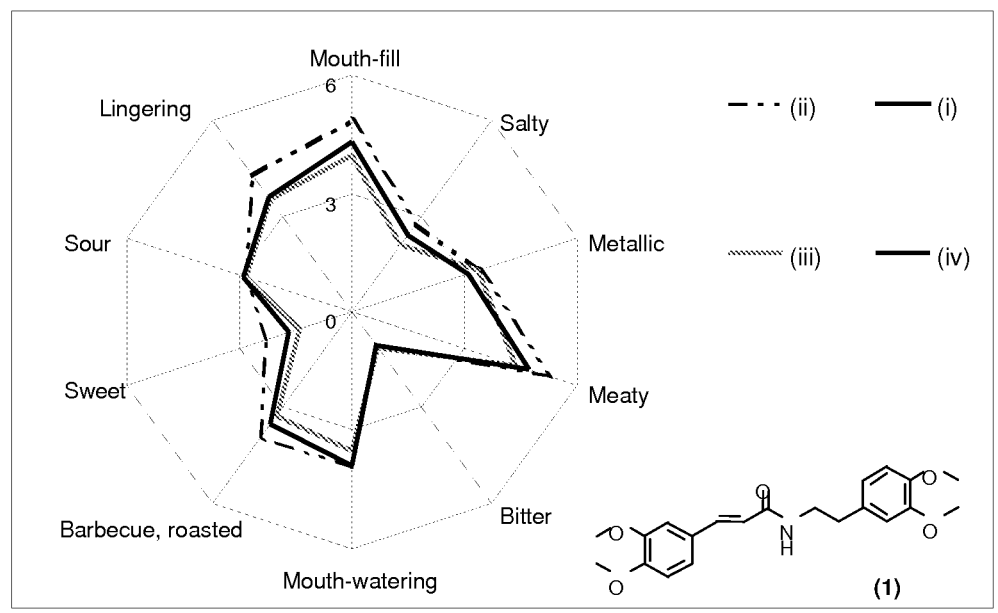
FIG. 1: Taste comparison between rubemamine (1) and monosodium glutamate.
Figure 2:
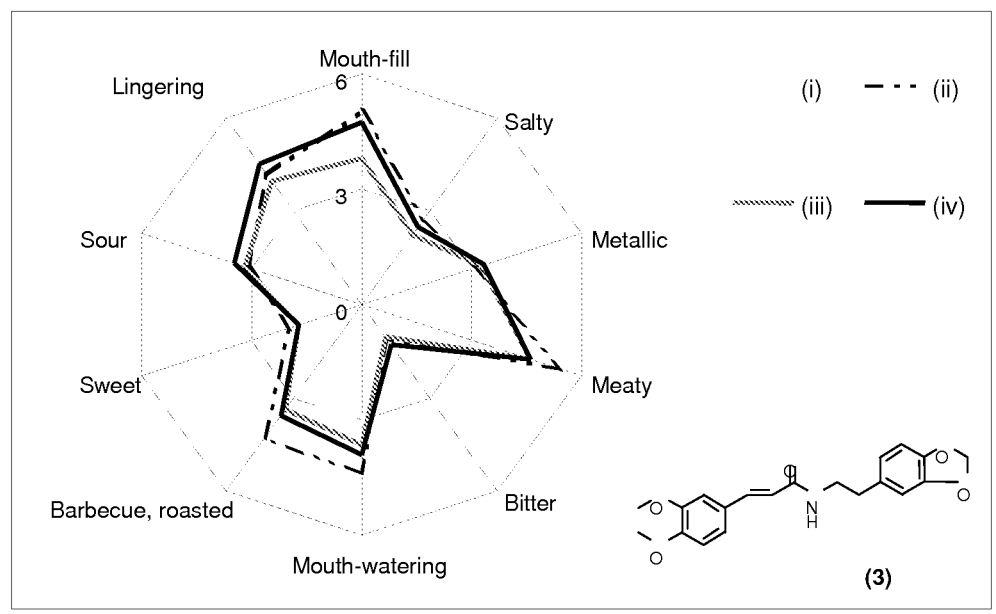

FIG. 2: Taste comparison of rubescenamine (3) and monosodium glutamate.

The taste of a 0.5% American beef extract as base (i) was compared in a tasting by a panel of trained test subjects with the taste of such a base with 5 ppm (iii) or 10 ppm (iv) rubescenamine (3) added, and such a base with 0.05 wt. % MSG added (ii).

The test subjects assessed the strength of the stated flavors by giving a score on a scale of 0 (imperceptible) through 9 (very strong corresponding taste). The mean values of the respective scorings are shown.

Figure 3:
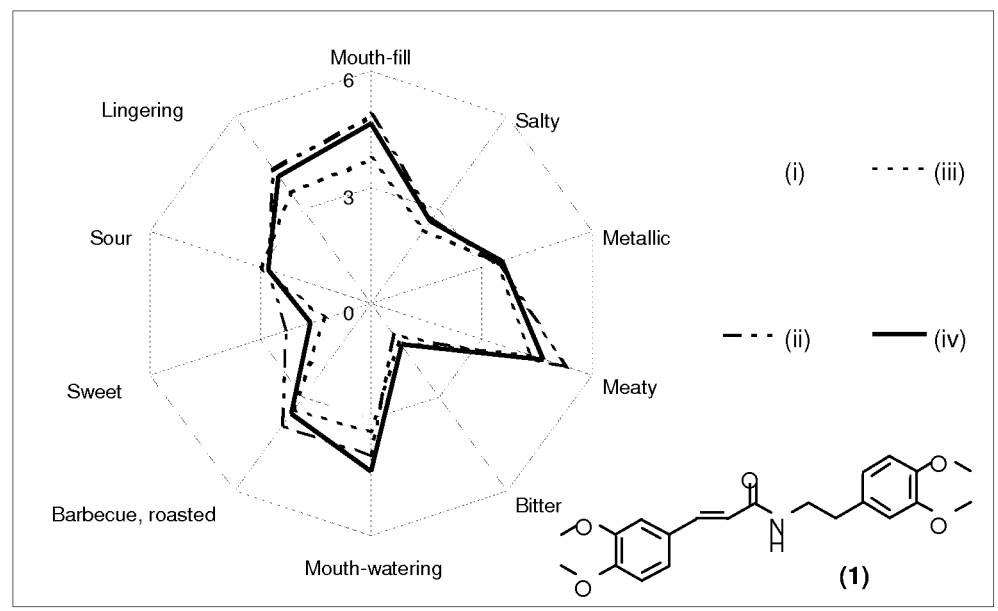

FIG. 3: Taste comparison of rubemamine (1) with a low monosodium glutamate-content beef extract.

The taste of a 0.5% American beef extract as base (i) was compared in a tasting by a panel of trained test subjects with the taste of such a base with 0.0025% monosodium glutamate (iii) added, such a base with 20 ppm rubemamine (1) and 0.0025% monosodium glutamate (iv) added, and such a base with 0.05 wt. % MSG added (ii).

The test subjects assessed the strength of the stated flavors by giving a score on a scale of 0 (imperceptible) through 9 (very strong corresponding taste). The mean values of the respective scorings are shown.

Figure 4:
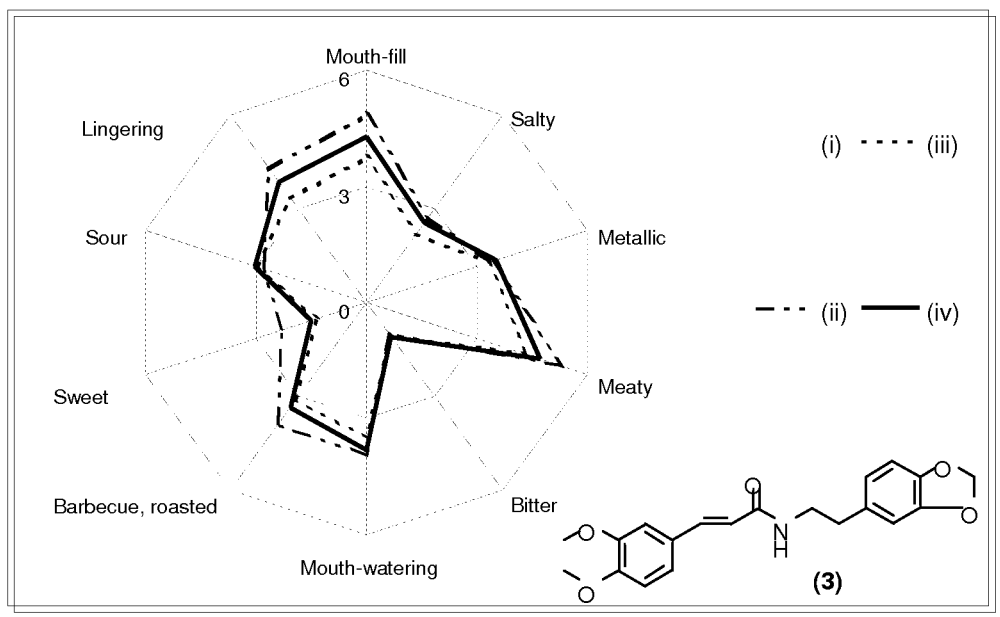

FIG. 4: Taste comparison of rubescenamine (3) with a low monosodium glutamate-content beef extract.

The taste of a 0.5% American beef extract as base (i) was compared in a tasting by a panel of trained test subjects with the taste of such a base with 0.0025% monosodium glutamate (iii) added, such a base with 20 ppm rubescenamine (3) and 0.0025 monosodium glutamate (iv) added, and such a base with 0.05 wt. % MSG added (ii).

The test subjects assessed the strength of the stated flavors by giving a score on a scale of 0 (imperceptible) through 9 (very strong corresponding taste). The mean values of the respective scorings are shown.

Figure 5:
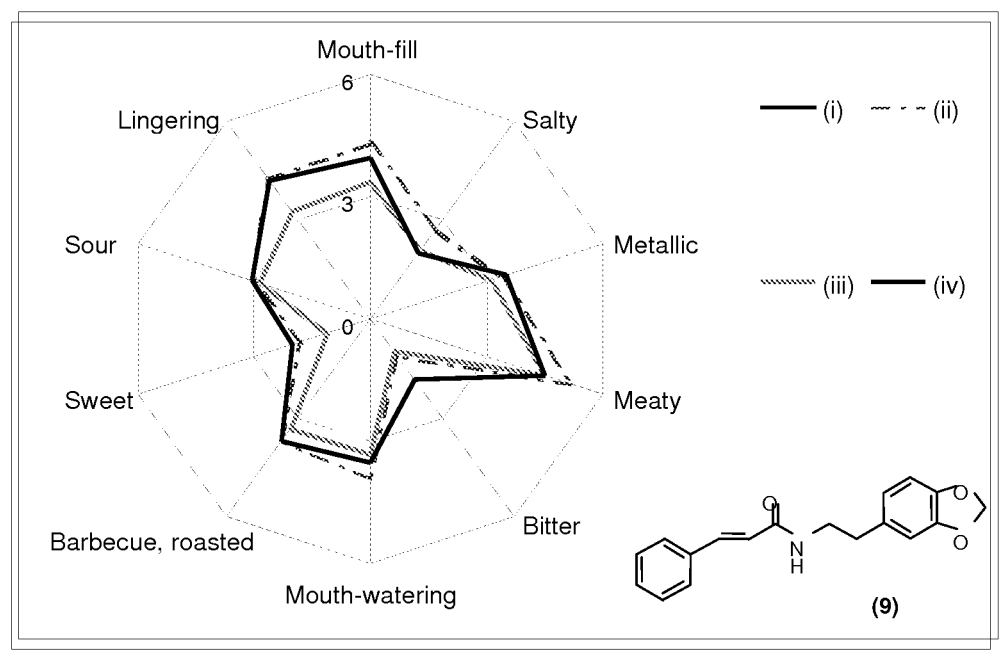

FIG. 5: Taste comparison of zanthomamine (9) with a low monosodium glutamate-content beef extract.

The taste of a 0.5% American beef extract as base (i) was compared in a tasting by a panel of trained test subjects with the taste of such a base with 0.0025% monosodium glutamate (iii) added, such a base with 20 ppm rubescenamine (3) and 0.0025% monosodium glutamate (iv) added, and such a base with 0.05 wt. % MSG added (ii).

The test subjects assessed the strength of the stated flavors by giving a score on a scale of 0 (imperceptible) through 9 (very strong corresponding taste). The mean values of the respective scorings are shown.

The invention claimed is:

1. A method for enhancing an umami taste comprising adding to a preparation:
   (a) one more compounds having an umami taste; and
   (b) one or more compounds of formula (I) in an amount sufficient to enhance the umami taste, wherein the one or more compounds of formula (I) is/are selected from the group consisting of:

Compound (1)

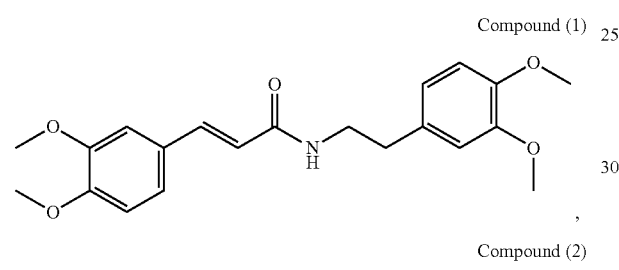
,

Compound (2)

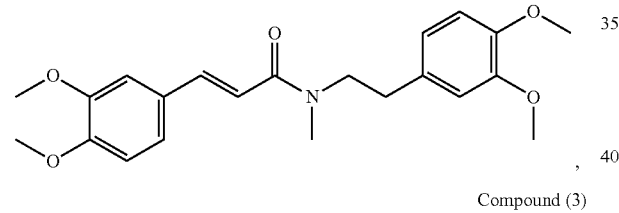
,

Compound (3)

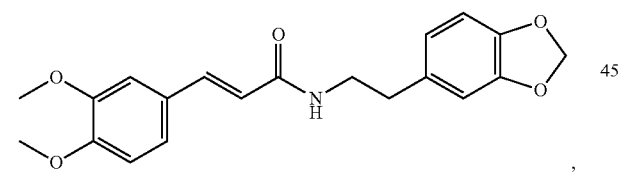
,

Compound (4)

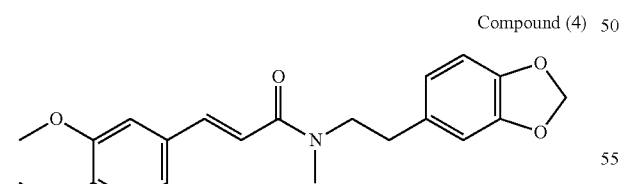
,

Compound (5)

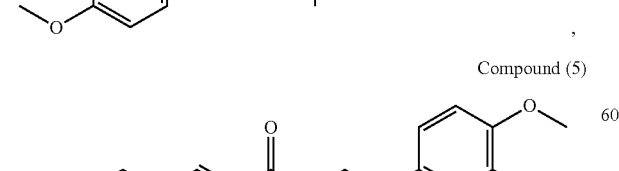
,

Compound (6)

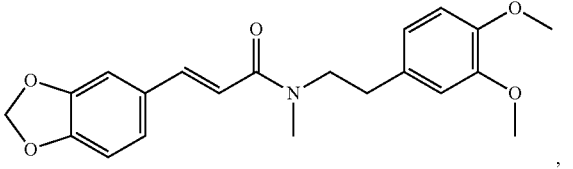
,

Compound (7)

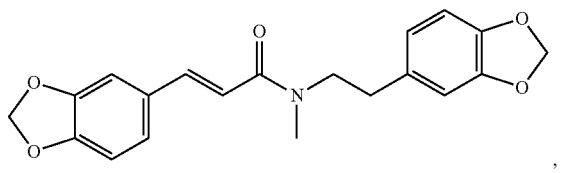
,

Compound (8)

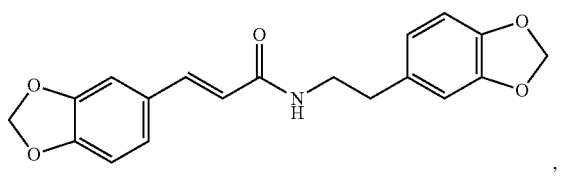
,

Compound (9)

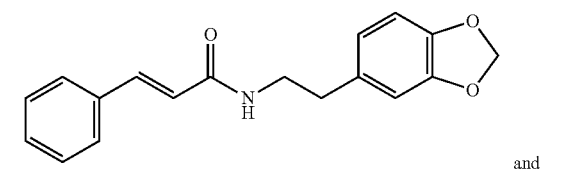

and

Compound (10)

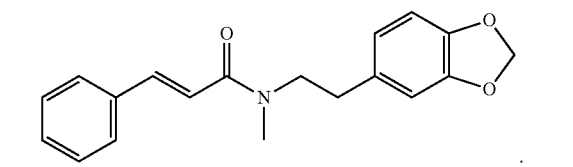
.

2. The method of claim 1, wherein one or more compounds having an umami taste are selected from the group consisting of monosodium glutamate, free glutamic acids, nucleotides or their pharmaceutically acceptable salts, strombines, theogallines, pyridin-betaine compounds, glutamic acid glycosides, malic acid glycosides, glutathione derivates, lactisoles and alkylpyridines, in particular 2-hexyl-, 2-heptyl and 2-octylpyridine, (2E,6Z)-N-cyclopropylnona-2,6-dienamide, (2E,6Z)-N-ethylnona-2,6-dienamide, N-[(2E)-3,7-dimethylocta-2,6-dienyl]cyclopropane carboxamide, N'-[(2-methoxy-4-methyl-phenyl)methyl]-N-[2-(5-methyl-2-pyridyl)ethyl]oxamide, N'-[(2,4-dimethoxyphenyl)methyl]-N-[2-(2-pyridyl)ethyl]oxamide, N'-[(2-methoxy-4-methyl-phenyl)methyl]-N-[2-(2-pyridyl)ethyl]oxamide, N-(1-propylbutyl)-1,3-benzodioxole-5-carboxamide, 1-(2-hydroxy-4-isobutoxy-phenyl)-3-(2-pyridyl)propan-1-one and 1-(2-hydroxy-4-methoxy-phenyl)-3-(2-pyridyl)propan-1-one.

3. The method of claim 2, wherein the one or more compounds having an umami taste comprise monosodium glutamate.

4. The method of claim 1, wherein the preparation is a vegetable extract.

5. The method of claim 4, wherein the vegetable extract is an extract of *Zanthoxylum rubescens* or *Chenopodium album*.

6. The method of claim 1, wherein (b) the total quantity of the one or more compounds of Formula (I) in relation to the total weight of the preparation is in the range of 5 ppm to 500 ppm.

7. The method of claim 1, wherein the preparation is a ready-to-use or ready-to-serve preparation for nutrition or pleasure.

8. The method of claim 7, wherein (b) the total quantity of the one or more compounds of Formula (I) in relation to the total weight of the ready-to-use or ready-to-serve preparation is in the range of 25 through 100 ppm.

9. The method of claim 1 comprising a mixture of compounds of formula (I).

10. The method of claim 9, wherein the mixture of compounds of formula (I) comprises Compound (1) and Compound (3):

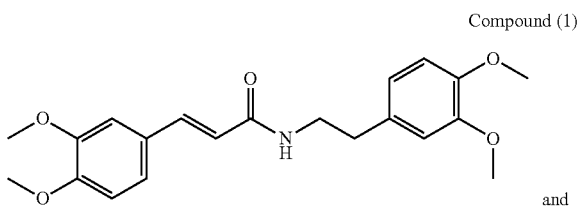

Compound (1)

and

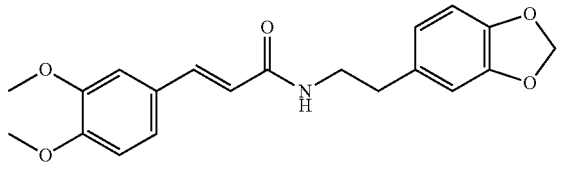

Compound (3)

11. The method of claim 1 further comprising:
(c) one or more compounds that mask or reduce an unpleasant taste.

12. The method of claim 11, wherein the unpleasant taste is a bitter, metallic, chalky, acidic, and/or metallic taste.

13. The method of claim 1 further comprising:
(d) one or more compounds that impart or enhance a sweet taste.

14. The method of claim 13, wherein the (d) one or more compounds that impart or enhance a sweet taste are selected from the group consisting of hesperetine, 3,7'-dihydroxy-4'-methoxyflavane, and phloretin.

15. The method of claim 14, wherein the (d) one or more compounds that impart or enhance a sweet taste is in an amount of 1 to 400 ppm, based on the total weight of the preparation.

16. The method of claim 1, where the preparation is a spray-dried preparation.

* * * * *